(12) United States Patent
Hedmann et al.

(10) Patent No.: US 8,673,139 B2
(45) Date of Patent: Mar. 18, 2014

(54) DIALYSIS MACHINE, IN PARTICULAR PERITONEAL DIALYSIS MACHINE

(75) Inventors: Frank Hedmann, Volksbach (DE); Sven Sebesta, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 430 days.

(21) Appl. No.: 12/929,049

(22) Filed: Dec. 23, 2010

(65) Prior Publication Data

US 2011/0186517 A1  Aug. 4, 2011

(30) Foreign Application Priority Data

Dec. 23, 2009 (DE) .......................... 10 2009 060 330

(51) Int. Cl.
*B01D 61/32* (2006.01)
*B01D 61/28* (2006.01)
*B01D 61/24* (2006.01)

(52) U.S. Cl.
USPC ............... 210/143; 210/85; 210/90; 210/97; 210/103; 210/109; 210/149; 210/175; 210/232; 210/252; 210/321.71

(58) Field of Classification Search
USPC ............... 210/85, 90, 97, 103, 109, 137, 143, 210/149, 175, 232, 233, 252, 321.71
See application file for complete search history.

(56) References Cited

U.S. PATENT DOCUMENTS

| | | |
|---|---|---|
| 2008/0015493 A1 | 1/2008 | Childers et al. |
| 2009/0009179 A1 | 1/2009 | Sobue et al. |
| 2009/0012452 A1 | 1/2009 | Slepicka et al. |
| 2009/0012455 A1 | 1/2009 | Childers et al. |
| 2009/0212178 A1 | 8/2009 | Westberg |

FOREIGN PATENT DOCUMENTS

| | | |
|---|---|---|
| EP | 1 669 051 A1 | 6/2006 |
| GB | 2 099 391 A | 12/1982 |
| GB | 2 362 843 A | 12/2001 |
| WO | WO 93/09820 A1 | 5/1993 |
| WO | WO 2007/144427 A2 | 12/2007 |
| WO | WO 2008/106452 A1 | 9/2008 |
| WO | WO 2009/006471 A2 | 1/2009 |
| WO | WO 2009/108405 A1 | 9/2009 |

*Primary Examiner* — John Kim
(74) *Attorney, Agent, or Firm* — Jacobson Holman PLLC

(57) ABSTRACT

A dialysis machine, in particular a peritoneal dialysis machine, to which a fluid system having a multi-chamber container with at least two chambers with individual solutions separated by a partition arrangement to be opened mechanically can be coupled includes a controller and at least one sensor for the determination of a measured variable in the fluid system. The controller has an apparatus for the automatic checking of the proper opening of the partition arrangement with reference to the measured variable determined by the sensor.

19 Claims, 16 Drawing Sheets

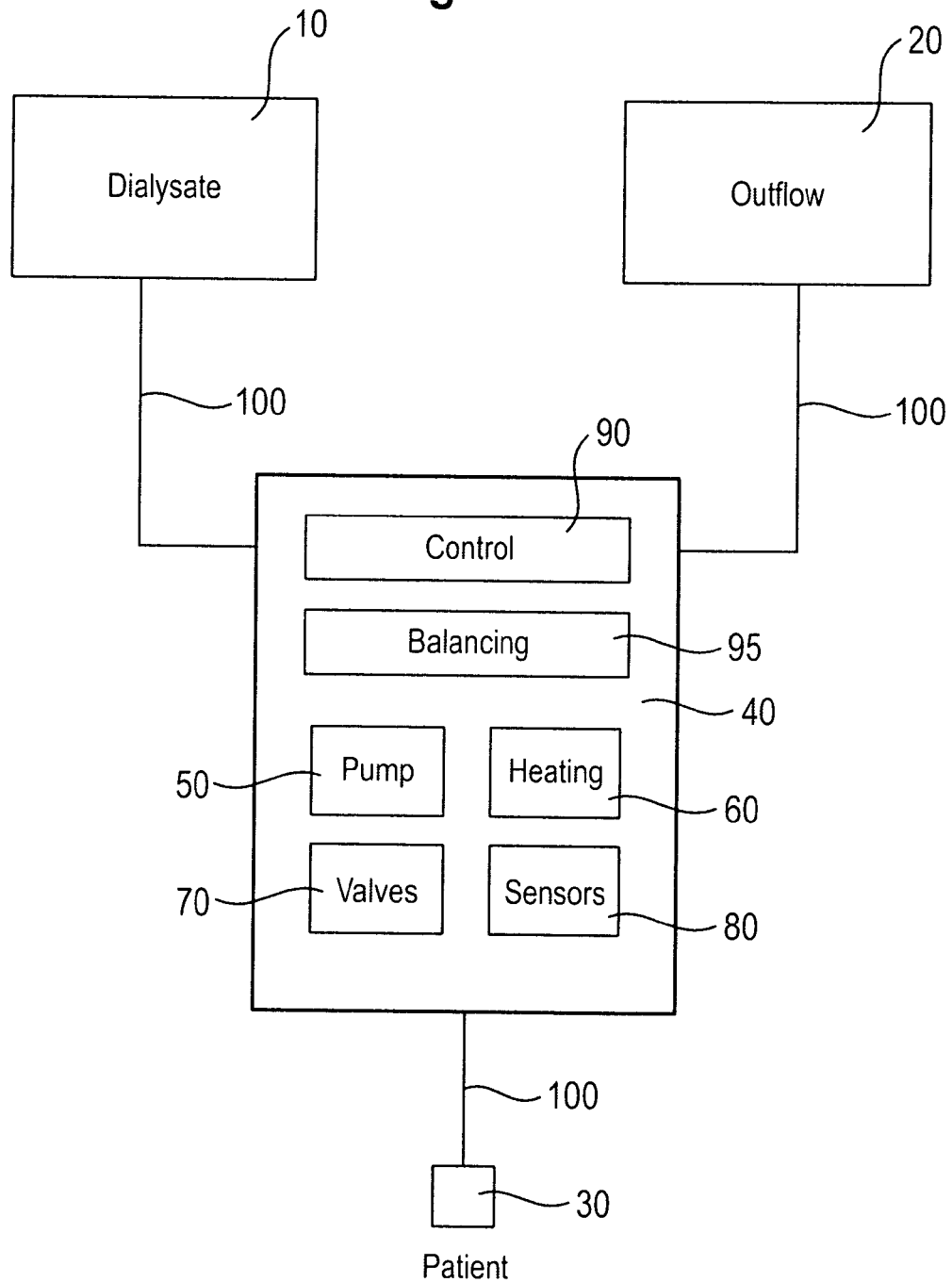

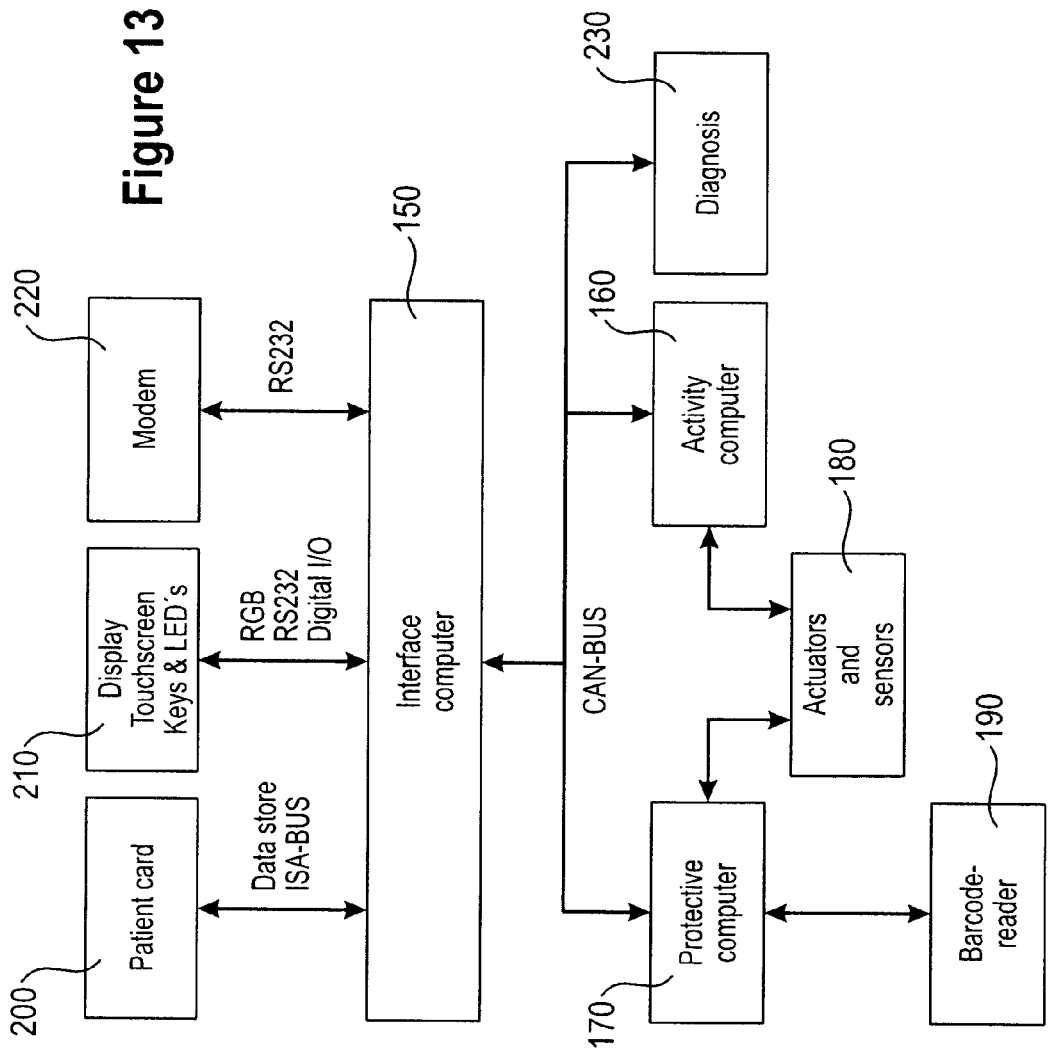

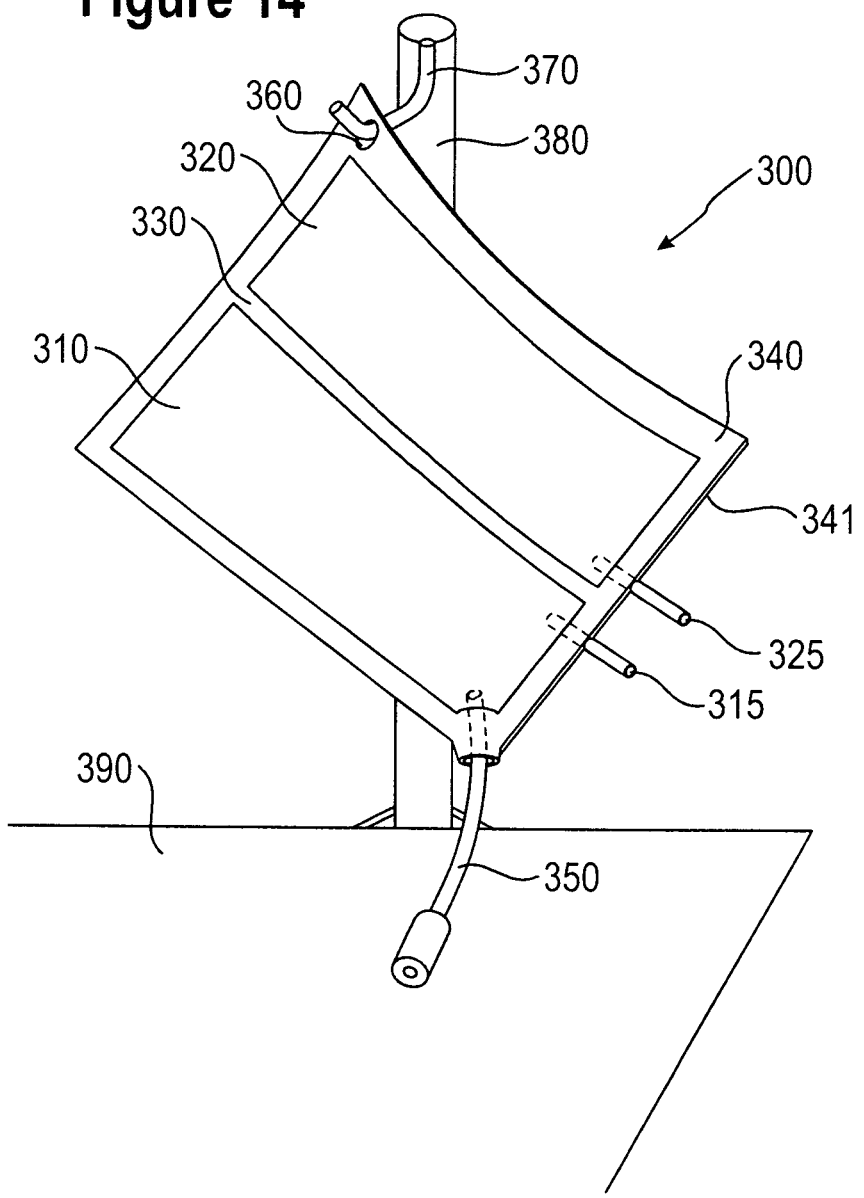

DIALYSIS MACHINE, IN PARTICULAR PERITONEAL DIALYSIS MACHINE

This application has a priority of German no. 10 2009 060 330.1 filed Dec. 23, 2009, hereby incorporated by reference.

BACKGROUND OF THE INVENTION

1. Field of Invention

The present invention relates to a dialysis machine, in particular a peritoneal dialysis machine, to which a fluid system can be coupled which has a multi-chamber container with at least two chambers comprising individual solutions and separated by a partition arrangement to be opened mechanically. The dialysis machine in this respect furthermore has a controller and at least one sensor for the determination of a measured variable in the fluid system.

2. Description of the Prior Art

In the field of dialysis, in particular in the field of peritoneal dialysis, it is usual to mix prepared individual solutions with one another only briefly before the treatment in order thus to provide a finished dialysis solution. This is due, on the one hand, to the fact that certain ingredients are incompatible for storage and unwanted waste products arise on storage in the mixed state. In addition, the heat sterilization of the solution in the mixed state is often problematic or not possible.

To ensure a simple handling of such solutions incompatible for storage, they are divided into individual solutions compatible for storage and are packed in a multi-chamber container which has at least two chambers. To ensure a simple combination of the individual solutions, the chambers are separated by a partition arrangement which can be mechanically opened. Briefly before the treatment, the partition arrangement is therefore manually opened by the patient or by an operator so that the individual solutions mix to form the desired dialysis solution.

Typically, a multi-chamber bag is used as the multi-chamber container in this respect. A seam which is easy to open and which is also called a peel seam is typically used as the partition arrangement for the division of the bag into a plurality of separate chambers. The seam is in this respect designed to be stable so that an unintentional opening of the seam and a combination of the individual solution associated therewith being able to be avoided during storage and transport. The peel seam between the chambers is then opened briefly before the treatment so that the at least two chambers combine to one single chamber and the previously separately stored individual solutions can mix with one another. In this respect, the opening takes place by the patient or by a user in that pressure is exerted onto at least one of the chambers, whereby the peel seam is opened.

After the opening of the partition arrangement, dialysis fluid can now be removed from the multi-chamber container. For this purpose, the multi-chamber container typically has an outflow, e.g. in the form of a hose arrangement. This is typically arranged in the region of one of the at least two chambers in known multi-chamber containers, in particular with multi-chamber bags. If the partition arrangement is therefore not opened properly, only one of the individual solutions flows out of the multi-chamber container. This can result in substantial risks for the patient since hereby the correct dialysis fluid, which comprises a mixture of the plurality of individual solutions, is not used, but rather an individual solution.

It is therefore known from the field of hemodialysis to dispense with the use of multi-chamber containers and to manufacture the total solution by separate pumping out of the individual solutions and an automatic mixing of the individual solutions by the dialysis machine. A conductivity sensor is typically used here which monitors the correct mixture of the total solution which arises.

In the field of peritoneal dialysis, the dialysate is, however, supplied directly from the abdomen of the patient so that substantially higher demands have to be made on the sterility of the dialysate. The use of conductivity sensors is therefore extremely problematic in the field of peritoneal dialysis. Multi-chamber containers having a partition arrangement to be opened mechanically are therefore in particular used in the field of peritoneal dialysis.

With known dialysis systems in which multi-chamber containers are used, an attempt is therefore made, e.g. via operator guidance with warning messages, to guide the operator to a more proper opening of the partition arrangement. In addition, partly mechanical designs of the multi-chamber container are known in which a discharge of fluid from the multi-chamber container only becomes possible after opening the partition arrangement. However, it has not yet been possible to achieve sufficient safety with known systems.

SUMMARY OF THE INVENTION

It is the object of the present invention to reduce the risks for the patient which arise by the use of a multi-chamber container having a partition arrangement to be opened mechanically.

This object is achieved in accordance with the invention by a dialysis machine as described herein. More specifically, the dialysis machine in accordance with the invention can be coupled to a fluid system comprising a multi-chamber container having at least two chambers with individual solutions which are separated by a partition arrangement to be opened mechanically. It is in this respect in particular a partition arrangement which can or must be opened manually by the patient or an operator. The dialysis machine furthermore has a controller with at least one sensor for the determination of a measured variable in the fluid system. Provision is made in this respect in accordance with the invention that the controller has an apparatus for the automatic checking of the proper opening of the partition arrangement of the multi-chamber container which automatically checks the proper opening of the partition arrangement of a multi-chamber container of a fluid system coupled to the dialysis machine with reference to the measured variable determined by the sensor. The risks for the patient associated with the partition arrangement which must be opened mechanically can be minimized by the automatic checking of the proper opening of the partition arrangement by the dialysis machine. The advantages of a multi-chamber container can hereby be utilized without having to accept the risks previously associated with this.

The apparatus in accordance with the invention for the automatic checking in this respect advantageously checks the proper opening of the partition arrangement of the multi-chamber container before liquid is taken from the multi-chamber container for the dialysis treatment. For peritoneal dialysis this means that the proper opening of the partition arrangement is checked before fluid is conducted from the multi-chamber container to the patient. It can hereby be precluded that an incorrectly mixed fluid is used for the dialysis treatment on a faulty opening.

The controller in this respect advantageously only starts the dialysis treatment when a proper opening of the partition arrangement was recognized. In a further advantageous manner, the controller outputs a signal to the user if an improper opening of the partition arrangement was recognized. The attention of the user is hereby drawn to the fact that the partition arrangement still has to be properly opened.

Alternatively or additionally, the apparatus in accordance with the invention for the automatic checking can also monitor the proper opening of the partition arrangement of the multi-chamber container during the course of the dialysis treatment. In this respect, the dialysis treatment is advantageously interrupted when an improper opening of the partition arrangement is detected.

Provision is made in a further advantageous manner that the sensor measures the measured variable in the fluid system without direct contact with the fluid in the fluid system. The direct contact of components of the dialysis machine with the fluid in the fluid system can hereby be avoided. This is in particular of great importance in peritoneal dialysis to ensure the sterility of the fluid in the fluid system. The complete fluid system can furthermore hereby be configured as a disposable article.

The sensor is in this respect advantageously arranged in the dialysis machine and is coupled to a sensor region of the fluid system on the coupling of the fluid system. The sensor can thus determine a measured variable in the fluid system without coming into direct contact with the fluid of the fluid system.

Advantageously, in accordance with the invention, it is a temperature sensor and/or a pressure sensor and/or a weight sensor and/or an optical sensor. None of these sensors has to come directly into contact with the fluid in the fluid system to determine a measured variable of the fluid system. A temperature value, a pressure value, a weight value or an optical property in the fluid system can in particular be determined in this respect.

Provision can be made in this respect that the dialysis machine in accordance with the invention determines the proper opening of a partition arrangement of the multi-chamber bag with reference to a measured value, in particular with reference to a query whether a measured value exceeds a specific limit value and/or is below a specific limit value.

Provision can alternatively or additionally be made that the apparatus for the automatic checking automatically checks the proper opening of the partition arrangement of the multi-chamber bag over time with reference to the change in the measured variable determined by the sensor. The measured variable is for this purpose determined at least two different times. The measured variable can in particular also be determined substantially continuously and the derivation of the measured variable can be determined in dependence on the time.

The checking of the proper opening in this respect advantageously takes place with reference to a query whether the change exceeds a specific limit value and/or whether the change is below a specific limit value.

The dialysis machine in this respect advantageously acts on the fluid system, in particular thermally and/or mechanically, before the determination of at least one measured value. In a further advantageous manner, a first measured value can be determined before such an action and a second measured value can be determined before or after such an action on the fluid system. The action on the fluid system in this respect advantageously takes place via a heating element, a valve actuator and/or a pump actuator of the dialysis machine.

In an embodiment of the invention, the sensor is arranged at a region of the fluid system through which fluid flows which was conducted out of the multi-chamber container, in particular at a hose region or at a cassette region of the fluid system.

The dialysis machine therefore first opens one or more valves in the fluid system and then checks a property of the fluid flowing out of the multi-chamber bag into the other fluid system.

Alternatively, the sensor can also measure a property of the fluid present in the multi-chamber container.

It can in this respect be determined in accordance with the invention with reference to the measured variable whether the partition arrangement was opened properly. A physical property of the fluid system is in particular advantageously determined in this respect which is influenced by the opening of the partition arrangement.

Provision can be made in a further advantageous manner that the apparatus for the automatic checking of the proper opening of the partition arrangement of the multi-chamber bag also checks the proper mixing of the individual solutions. The proper mixing in this respect usually takes place in that the container is moved accordingly after the opening of the partition arrangement. However, the mixing also takes place automatically by diffusion with an open partition arrangement so that the apparatus in accordance with the invention for the automatic checking of the proper opening of the partition arrangement does not necessarily have to check the proper mixing of the individual solutions directly. The safety is, however, obviously increased when the measured variable depends not only on the opening of the partition arrangement, but also on the mixing of the individual solution.

In a first embodiment variant in the dialysis machine, it has a heating for the heating of the fluid in the multi-chamber container, with a first chamber of the multi-chamber container being heated and a second chamber not being heated for the checking of the proper opening of the partition arrangement of the multi-chamber container, with the check taking place by determination of a temperature and/or of a temperature change in the fluid system.

The heating of the dialysis machine in particular has two separate heating regions in this respect with which two chambers of the multi-chamber container are associated. To check the proper opening of the partition arrangement, only one of the two heating regions and thus only one of the two chambers are now heated for a specific time period. It can now be determined by determining the temperature or the temperature change in at least one of the chambers during or after this heating process whether the partition arrangement was opened properly and whether the two chambers are in fluid communication.

The heating of the dialysis machine in this respect advantageously has a heating surface onto which the multi-chamber container, in particular the multi-chamber bag, can be placed. The heating surface in this respect has at least two heating regions which can be heated separately from one another and onto which the corresponding chambers of the multi-chamber container are placed.

In a further advantageous manner, the dialysis machine has a temperature sensor which is associated with the first chamber and via which the temperature of the fluid in the region of the first chamber can be determined. Alternatively or additionally, the dialysis machine has a temperature sensor which is associated with the second chamber and via which the temperature of the fluid in the region of the second chamber can be determined. The corresponding sensor can in this respect be arranged on the heating surface of the heating and be in contact with the corresponding region of the multi-chamber container. Alternatively, the temperature of the fluid flowing out of the first chamber or out of the second chamber of the multi-chamber container can also be determined.

The checking of the proper opening of the partition arrangement in this respect advantageously takes place by a query whether the temperature of the fluid in the second chamber has exceeded a certain temperature threshold and/or whether the change in the temperature of the fluid in the second chamber is above a certain limit value. If the partition arrangement is not properly open, the two chambers are not in sufficient fluid communication. The fluid in the second chamber is hereby not heated or only heated a little by the heating of the region of the first chamber.

Alternatively or additionally, the checking takes place by a query whether the temperature of the fluid in the first chamber has remained below a certain temperature threshold and/or whether the change in the temperature of the fluid in the first chamber is below a certain limit value. If the partition arrangement was not properly opened, there is no sufficient fluid communication between the two chambers. The amount of fluid which is heated by the heating in the region of the first chamber is correspondingly smaller. The fluid in the region of the first chamber is hereby heated faster. This can in turn be used for the recognition of an improper opening of the partition arrangement.

In a further embodiment of the present invention, the checking of the proper opening of the partition arrangement takes place by determining an optical property of the fluid in the fluid system. The proper opening of the partition arrangement can also hereby be checked via a corresponding optical sensor.

The individual solutions are in this respect advantageously designed such that an optical property of a first individual solution is changed by the mixing with a second individual solution. The determination of the optical property can in this respect likewise take place without any direct contact of the sensor with the fluid. The determination of the optical property of the fluid furthermore also allows a verification of whether a proper mixing of the fluids has taken place.

Advantageously in accordance with the invention, the color and/or the brightness and/or the polarization properties of the fluid present in the multi-chamber container or flowing out of the multi-chamber container is/are determined as the optical property.

Provision can advantageously be made that the color and/or cloudiness of a first individual solution changes by the mixing with a second individual solution. Provision can in particular be made that at least one of the individual solutions in the multi-chamber container is dyed so that a color change of at least one of the individual solutions results by the mixing with another individual solution. In this respect, the individual solution in the chamber in whose region the outlet for the removal of the total solution is arranged is advantageously not dyed, whereas a second individual solution in a further chamber is dyed. If the partition arrangement is not properly opened, no mixing takes place and the outflowing solution is still clear. If, in contrast, the partition arrangement was opened, the total solution is dyed. The proper opening can therefore e.g. be recognized via a cloudiness sensor.

Provision can alternatively or additionally be made that the polarization properties of a first individual solution change by the mixing with a second individual solution. The sensor then advantageously determines the polarization properties of the fluid in the multi-chamber bag or advantageously those of the fluid flowing out of the multi-chamber bag.

The present invention further includes a multi-chamber container having at least two chambers separated by a partition arrangement to be opened mechanically. A partition arrangement can in particular be opened manually by the patient or by an operator in this respect. The present invention in this respect in particular includes a multi-chamber bag having at least two chambers separated by a peel seam to be opened mechanically. Provision is made in this respect in accordance with the invention that the two chambers contain different individual solutions and an optical property of a first individual solution changes by mixing with a second individual solution.

The optical property can in particular be the color of the individual solution. In this respect, in particular only a second solution is dyed which is present in a chamber in which the outflow is not arranged. The dye is in this respect a dye which is not of any danger to the health.

Provision can alternatively or additionally be made that the optical property which changes by the mixing with the second individual solution is a polarization property of the individual solution. The proper opening of the partition arrangement and the mixing of the individual solutions can hereby be checked by determining this polarization property without the individual solutions having to be visibly dyed for the operator.

In a further embodiment of the dialysis machine in accordance with the invention, the checking of the proper opening of the partition arrangement takes place by determination of a pressure or of a pressure change in the fluid system. In this respect, the opening of the partition arrangement has an influence on the pressure of the fluid in the multi-chamber container or on the pressure which the fluid exerts on a pressure measuring region of the fluid system in the multi-chamber container. The check in particular takes place in this respect with reference to the hydrostatic pressure of the fluid in the multi-chamber container or from the multi-chamber container.

At least one valve region of the fluid system is advantageously opened in this respect so that the multi-chamber container is in fluid communication with the pressure measuring region of the fluid system. A pressure sensor of the dialysis machine there determines the hydrostatic pressure of the fluid and draws a conclusion on the configuration of the multi-chamber container from this pressure or from a pressure change.

The multi-chamber container is advantageously arranged at the dialysis machine in this respect such that the hydrostatic pressure at the outflow with a closed partition arrangement differs from the hydrostatic pressure with an open partition arrangement. This can in particular be achieved in that the fluid level in the chamber at which the outflow is arranged is lower or higher with a closed partition arrangement than the fluid level in the total chamber which forms after the opening of the partition arrangement.

Provision can in particular be made in this respect that the fluid level in a first chamber is arranged higher with a closed partition arrangement than the fluid level in a second chamber. The hydrostatic pressure at the outflow hereby changes when the partition arrangement was opened.

The multi-chamber container is in this respect in particular a multi-chamber bag which is hung at a stand in a first marginal region and in which the outflow for the fluid is arranged in a second marginal region disposed substantially opposite. The partition seam in this respect advantageously extends transversely between the first and second regions so that the hydrostatic pressure at the outlet of the multi-chamber bag increases by opening the partition seam.

The dialysis machine in this respect advantageously has a connection arrangement for the connection of the multi-chamber container to the dialysis machine, in particular a hook for the hanging of a multi-chamber bag. A defined height difference between the multi-chamber container and the pressure sensor system of the dialysis machine can hereby be established. The connection arrangement can in this respect e.g. be arranged at a rack on which the actual dialysis machine is arranged.

The determination of the pressure in this respect advantageously takes place via a pressure sensor for the determination of the pressure in a region of the fluid system, in particular in a chamber of a cassette of the fluid system. The determination of the pressure can in this respect take place directly by coupling of a pressure sensor to the region of the fluid system, in particular to the chamber, or by determination of a pressure in a hydraulic system of an actuator which is coupled to the region of the fluid system, in particular to the chamber of the cassette. Alternatively to the coupling of the pressure sensor to a chamber of a cassette, the pressure sensor can also be coupled to the tubing set. This is in particular the case when no cassette is inserted, but the dialysate is rather pumped into the abdomen of the patient via a controllable clamping apparatus and a hose pump. The determination of the hydrostatic pressure can e.g. take place via a pressure measurement device anyway present in the dialysis machine, in particular via a pressure sensor associated with a pump chamber. The dialysis machine can in this respect bring the pump chamber into fluid communication with the multi-chamber bag for the checking of the proper opening of the partition arrangement and can recognize by determination of the hydrostatic pressure in the pump chamber whether the partition arrangement was properly opened.

The measurement can in this respect take place in that a balance is adopted between the pressure which arises by the dialysate in the pump chamber and the pressure which is produced by a hydraulic fluid used for the movement of a pump membrane of the pump chamber. The pressure in the pump chamber can thus be measured by a sensor on the hydraulic side since the pressure there corresponds due to the balance to the pressure on the dialysate side. Alternatively, the pressure due to the dialysate can also be measured by a sensor which is coupled directly to a chamber in fluid communication with the multi-chamber bag.

In a further embodiment of the dialysis machine in accordance with the invention, provision can be made that the checking takes place by determination of the weight and/or of the change in the weight of the multi-chamber bag. A weighing unit is in particular provided for this purpose via which the weight of the multi-chamber container can be determined. The opening of the partition arrangement in this respect has an influence on the flow rate from the multi-chamber container which can be determined via the weight of the multi-chamber container.

In a further advantageous manner, provision can be made in the dialysis machine in accordance with the invention that the checking of the proper opening of the partition arrangement is determined by determination of the flow rate of the fluid flowing out of the multi-chamber container. The determination of the flow rate can in this respect in particular take place via the above-described determination of the weight or of the change in the weight of the multi-chamber container. Alternatively or additionally, the determination of the flow rate can also take place via other balancing means of the dialysis machine.

In a further embodiment of the dialysis machine in accordance with the invention, the checking takes place by an ultrasonic sensor system, in particular via a reflection ultrasonic sensor system. The proper opening of the partition arrangement can in this respect in particular take place by the detection of a reflection characteristic. Provision can furthermore be made that the checking takes place by means of the ultrasonic sensor system with reference to a filling level recognition. The checking can in this respect take place via an absolute filling level and/or with reference to a filling level change in the multi-chamber container.

Provision can furthermore be made that the checking takes place with reference to a change in the reflection characteristic which is caused by the opening of the partition arrangement. In particular an opening of the partition arrangement can thus be checked which takes place after the coupling of the multi-chamber container to the dialysis machine. This is particularly suitable for the checking of an automatic opening of the partition arrangement by the dialysis machine.

The ultrasonic sensor system can in this respect already be coupled to a chamber of the multi-chamber container on the coupling of the multi-chamber container to the dialysis machine. In this case, e.g. a change in the reflection properties of this chamber can be used for checking on the opening of the partition arrangement. Alternatively, a coupling of the ultrasonic sensor system can also only take place by a change in the shape of the multi-chamber bag which is caused by the opening of the partition arrangement. If the signal of the ultrasonic sensor system in this case corresponds to that of a coupled chamber, a conclusion on the proper opening can be drawn via this.

The present invention furthermore comprises a dialysis machine, in particular a peritoneal dialysis machine, to which a fluid system can be coupled which has a multi-chamber container with at least two chambers comprising individual solutions and separated by a partition arrangement to be opened mechanically, having a controller. Provision is made in this respect that the dialysis machine has means for the automatic opening of the partition arrangement. It is hereby ensured that the partition arrangement was properly opened before the start of the treatment since this opening is carried out by the machine itself. The user of the machine therefore no longer has to open the partition arrangement manually him or herself.

Such means for the automatic opening of the partition arrangement are obviously also of great advantage independently of the above-described apparatus for the automatic checking of the proper opening of the partition arrangement of the multi-chamber container and are therefore also an independent subject of the present invention independently thereof. However, particular advantages result when the means for the automatic opening of the partition arrangement is combined with the above-described apparatus for the automatic checking of the proper opening of the partition arrangement of the multi-chamber container.

The means for the automatic opening of the partition arrangement advantageously have means for building up pressure in at least one chamber of the multi-chamber container. The partition arrangement can hereby be reliably opened by the dialysis machine. The build-up of pressure in this respect advantageously takes place via a line via which the chamber of the multi-chamber bag was connected to the dialysis machine, in particular in that a fluid, i.e. a gas or a liquid, is pumped into the chamber.

The pressure build-up advantageously takes place via the introduction of compressed air or via the pumping of liquid into the chamber. The compressed air can in this respect be taken from the anyway present compressed air of the pneumatic system of the dialysis machine. On the use of compressed air, this is advantageously purified via a sterile filter. If the pressure increase is generated via the pumping of liquid into the chamber, it can be taken from a further chamber of the multi-chamber container or from a chamber of a further multi-chamber container.

The controller advantageously includes an apparatus for the automatic checking of the proper opening of the partition arrangement of the multi-chamber container which checks the proper opening of the partition arrangement by the means for the automatic opening.

This checking can in particular take place with reference to a pressure and/or to a pressure development and/or to a filling quantity. A certain overpressure is in this respect usually necessary in the pressurized chamber to open the partition arrangement. The apparatus for the monitoring can now check whether a pressure drop is taking place by the opening of the partition arrangement after the exceeding of this pressure. The apparatus for the monitoring can furthermore check the characteristic of the pressure increase to recognize whether the partition arrangement was not already opened beforehand. In this respect, the apparatus can likewise check whether the pressure after the exceeding of the pressure required for the opening still increases above a second, higher limit value without a pressure drop taking place. If the pressure is generated by the pumping of liquid, the quantity of pumped liquid can additionally be monitored and optionally evaluated together with the pressure.

In accordance with the invention, the partition arrangement can be opened by the application of pressure generated by the dialysis machine to a fluid in a first chamber. At the moment of opening the partition arrangement, a measurable pressure drop occurs due to the enlarged volume through the additional chamber. It can be verified by this pressure drop that the partition arrangement was opened. It is likewise possible in this respect to detect that a plurality of partition arrangements were opened since a specific pressure development hereby results which is dependent on the type of the partition arrangements.

The present invention furthermore includes a dialysis machine having a fluid system with a multi-chamber container with at least two chambers having individual solutions separated by a partition arrangement to be opened mechanically, with the dialysis machine and the fluid system being structured as shown in more detail above.

The present invention furthermore includes a method for the operation of a dialysis machine, in particular a peritoneal dialysis machine, comprising the steps:
  coupling a fluid system having a multi-chamber container to at least two chambers separated by a partition arrangement to be opened mechanically;
  determining a measured variable in the fluid system via a sensor of the dialysis machine; and
  checking the proper opening of the partition arrangement of the multi-chamber container of the fluid system coupled to the dialysis machine with reference to the measured variable.

As was already presented above, it can hereby be ensured that the partition arrangement was opened properly and the correct total solution for the dialysis treatment is used.

It is in this respect advantageously a method for the operation of a dialysis machine, as was presented above, and in particular a method for the upgrading of a dialysis machine. The dialysis machine in this respect automatically checks the proper opening of the partition arrangement.

The method in this respect advantageously includes the triggering of an alarm and/or the prevention of a start of the treatment if the measured variable does not correspond to a measured variable expected on a proper opening of the partition arrangement, in particular when the measured variable is outside a preset range or below or above a limit value or if the development of the measured variable does not correspond to an expected development.

The present invention furthermore includes a method for the operation of a dialysis machine comprising the steps: coupling a fluid system having a multi-chamber container having at least two chambers separated by a partition arrangement to be opened mechanically and automatic opening of the partition arrangement by the dialysis machine.

The automatic opening of the partition arrangement in this respect advantageously takes place as was described above with respect to the dialysis machine. The method is in particular a method for the operation of an above-described dialysis machine.

In addition to the automatic opening, an automatic checking is advantageously provided in this respect as was likewise described above.

The present invention will now be described in more detail with reference to embodiments and drawings.

BRIEF DESCRIPTION OF THE DRAWINGS

FIG. 2 a schematic diagram of a peritoneal dialysis system;

FIG. 13 a schematic diagram of the design of an embodiment of a controller;

FIG. 14 an embodiment of a multi-chamber container which can be coupled to an embodiment of a dialysis machine in accordance with the invention;

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The function of a dialysis machine in which the present invention is used will first be described generally in the following. The dialysis machine in this embodiment is in this respect a peritoneal dialysis machine. The components described below can, however, also be used in the same manner or in a similar manner for a hemodialysis machine.

Peritoneal dialysis is a variant of artificial hemodialysis in which the peritoneum of the patient which has a good blood supply is used as a filter membrane natural to the body. Dialysate is introduced into the abdominal cavity via a catheter for this purpose. In accordance with the principle of osmosis, urea components of the blood now diffuse through the peritoneum into the dialysate present in the abdominal cavity. After a specific dwell time, the dialysate with the urea components is again eliminated from the abdominal cavity.

In automatic peritoneal dialysis, a dialysis machine controls and monitors the introduction of the fresh dialysate into the abdominal cavity and the elimination of the consumed dialysate. Such a dialysis machine, also called a cycler, in this respect usually fills and voids the abdominal cavity several times overnight, i.e. while the patient is asleep.

Figure 1A:
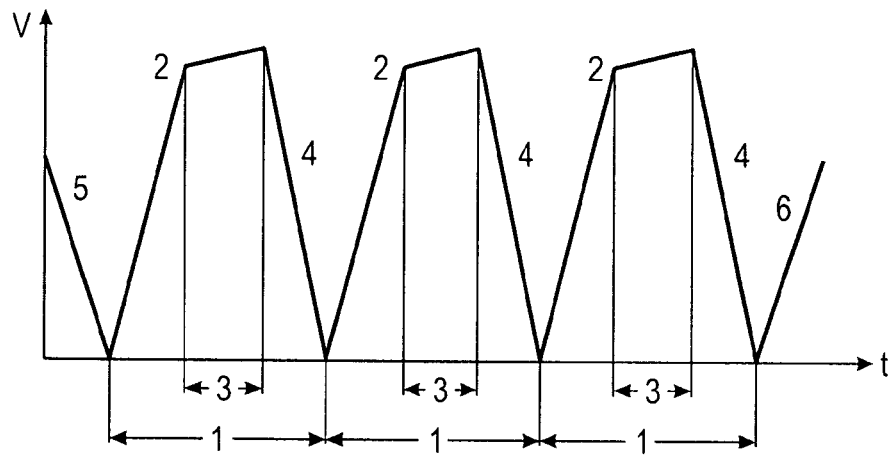
FIG. 1 three diagrams which show typical developments of an automatic peritoneal dialysis treatment.
Figure 1B:
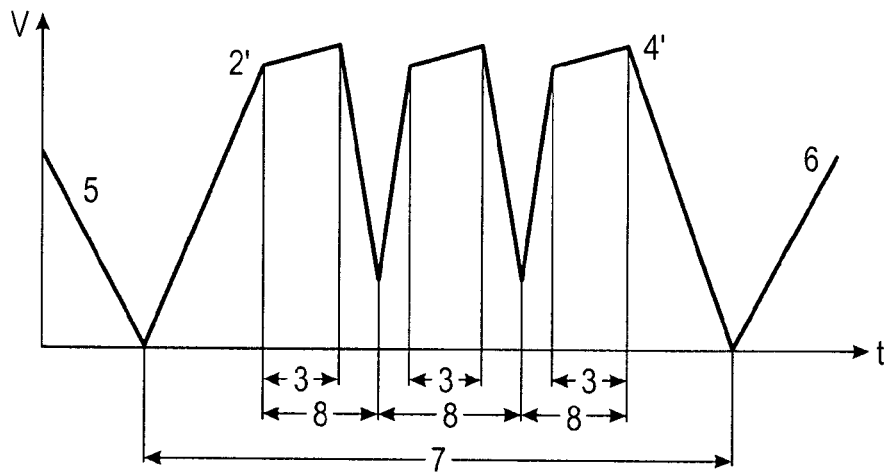
Figure 1C:
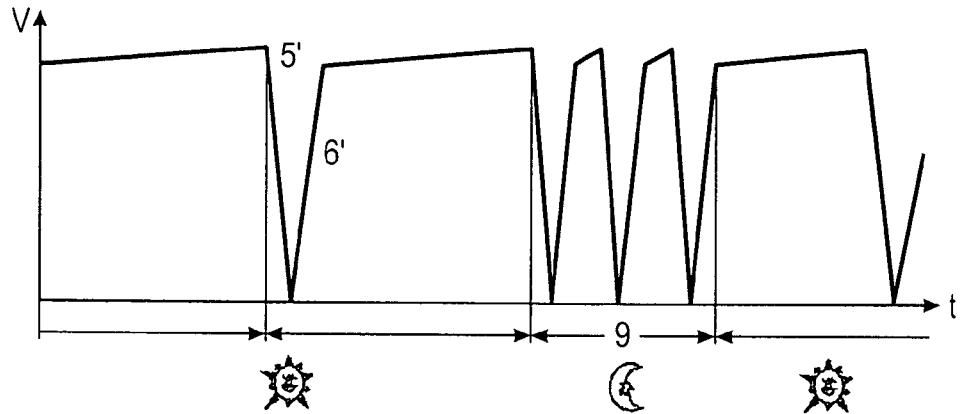

In FIGS. 1a to 1c, three different method procedures are shown such as are carried out by a dialysis machine. One of more of these process procedures is in this respect usually stored in the controller of the dialysis machine. It is usually possible in this respect to adapt the stored process procedures to the patient.

In FIGS. 1a to 1c, the dialysate quantity V respectively present in the patient's abdominal cavity is entered over the time t. In this respect, FIG. 1a shows the development of a normal automatic peritoneal dialysis treatment overnight. At the start of the treatment, an initial outflow 5 first takes place in this respect through which dialysate which was left in the abdominal cavity of the patient over the day is removed. A plurality of treatment cycles 1 then takes place; in FIG. 1a, three sequential treatment cycles 1. Each treatment cycle in this respect comprises an inflow phase 2, a dwell phase 3 and an outflow phase 4. In this respect, a specific volume of fresh dialysate fluid is introduced into the patient's abdominal cavity during the inflow phase 2. The maximum permitted dialysate quantity in this respect amounts to between approximately 1.5 and 3 l depending on the patient. The fresh dialysate now remains in the abdominal cavity for a specific dwell time 3. The dwell phase in this respect typically lasts some hours. The now consumed dialysate is then removed from the abdominal cavity again in the outflow phase 4. A new treatment cycle then starts. The treatment is concluded with a last inflow 6 by which a specific quantity of fresh dialysate is introduced into the patient's abdominal cavity. It then remains in the patient's abdominal cavity over the day.

The individual treatment cycles 1 which take place overnight are in this respect automatically controlled by the controller of the dialysis machine. The initial outflow and the last inflow can likewise be controlled automatically by the dialysis machine. Alternatively, they are activated manually by an operator or by the patient.

A so-called tidal treatment is shown in FIG. 1b. This also starts with an initial outflow 5 and ends with a last inflow 6. A base cycle 7 is furthermore provided which is divided into a plurality of tidal cycles 8. In this respect, a base inflow phase 2' is initially provided. After the dwell time 3, however, the complete dialysate volume is no longer removed from the abdominal cavity, but rather only a certain part quantity of the dialysate present in the abdominal cavity. This is then replaced by a corresponding volume of fresh dialysate. After a further dwell cycle, a further tidal removal can take place in which the total dialysate present in the abdomen is not removed. At the end of the base cycle 7, a base outflow phase 4' takes place in which the total dialysate is now removed. Only one base cycle 1 is in this respect shown in FIG. 1b. Alternatively, however, a plurality of base cycles can also be provided.

The course of a peritoneal dialysis treatment with a so-called PD plus treatment is shown in FIG. 1c. In this respect, a conventional peritoneal dialysis treatment takes place during the night 9 which can e.g. be carried out in accordance with the FIG. 1a or 1b. An additional PD plus treatment is, however, furthermore provided during the day in which the consumed dialysate is removed in an outflow phase 5' and is replaced by fresh dialysate in an inflow phase 6'. In the PD plus treatment, a normal night-time peritoneal dialysis treatment is combined with one or more additional treatment cycles during the day. The course of the night-time treatment is in this respect carried out as customary automatically by the dialysis machine. The treatment cycles during the day are likewise carried out and monitored via the machine.

The design of a typical peritoneal dialysis system is now shown schematically in FIG. 2. The peritoneal dialysis system in this respect includes a container 10 with fresh dialysate and an outflow 20 for used dialysate. A connector 30 is furthermore provided which can be connected to a catheter of the patient either to introduce fresh dialysate into the abdominal cavity of the patient or to remove consumed dialysate from the abdominal cavity. The container 10 with fresh dialysate, the outflow 20 for used dialysate and the connector 30 to the patient are in this respect connected to one another via fluid paths 100 and form the fluid system of the peritoneal dialysis system together with them.

A dialysis machine 40, also called a cycler, is provided for the carrying out of the peritoneal dialysis treatment. The dialysis machine 40 in this respect includes the following main components:

- A pump 50 which is used for the transport of the fluids. The pump 50 in this respect conveys the fresh dialysate from the container 10 to the connector 30. The pump 50 can furthermore transport the consumed dialysate from the connector 30 to the outflow 20.
- Valves 70 which are used for the control of the fluid flows. The valves 70 open and close the fluid paths 100 in order thus to establish the corresponding fluid connections between the container 10, the connector 30 and the outflow 20.
- A heating 60 which brings the fresh dialysate to a temperature of approximately 37° C. before it is supplied to the patient. Since relatively large quantities of dialysate are supplied directly into the abdominal cavity of the patient in peritoneal dialysis, the heating 60 is necessary in order not to cool the patient too much and to avoid an unpleasant feeling by dialysate which is too cold.
- Sensors 80 via which the proper procedure of the treatment can be monitored and/or controlled. Temperature sensors can in particular be used in this respect. Pressure sensors can furthermore optionally be used.

All the components of the dialysis machine 40 are in this respect controlled via a controller 90. In this respect, the controller 90 in particular controls the pump 50, the heating 60 and the valves 70 on the basis of the data of the sensors 80. The controller 90 in this respect provides the automatic procedure of the peritoneal dialysis. The controller 90 in this respect includes as an important component a balance 95 which balances the fluid quantities supplied to and removed from the patient. The balance in this respect prevents the patient from being given too much fluid or having too much fluid removed.

The balance 95 can in this respect take place solely on the basis of the control data and/or the sensor data for the pump

50. Alternatively, the balance can also take place via separately provided balancing chambers. It is equally possible to use scales for the balancing. Such scales, for example, weigh the weight of the container 10 with fresh dialysate and/or a container 20 with used dialysate.

Since the dialysate is dispensed to the patient directly into the abdominal cavity in peritoneal analysis, extreme sterility must be observed. The fluid paths or the fluid system which come into contact with the fresh dialysate and/or the used dialysate are therefore usually designed as disposable parts. The fluid paths or the fluid system are in this respect in particular designed as plastic parts. They can thus be supplied in a sterile outer packaging and only unpacked briefly before the treatment.

Figure 3:
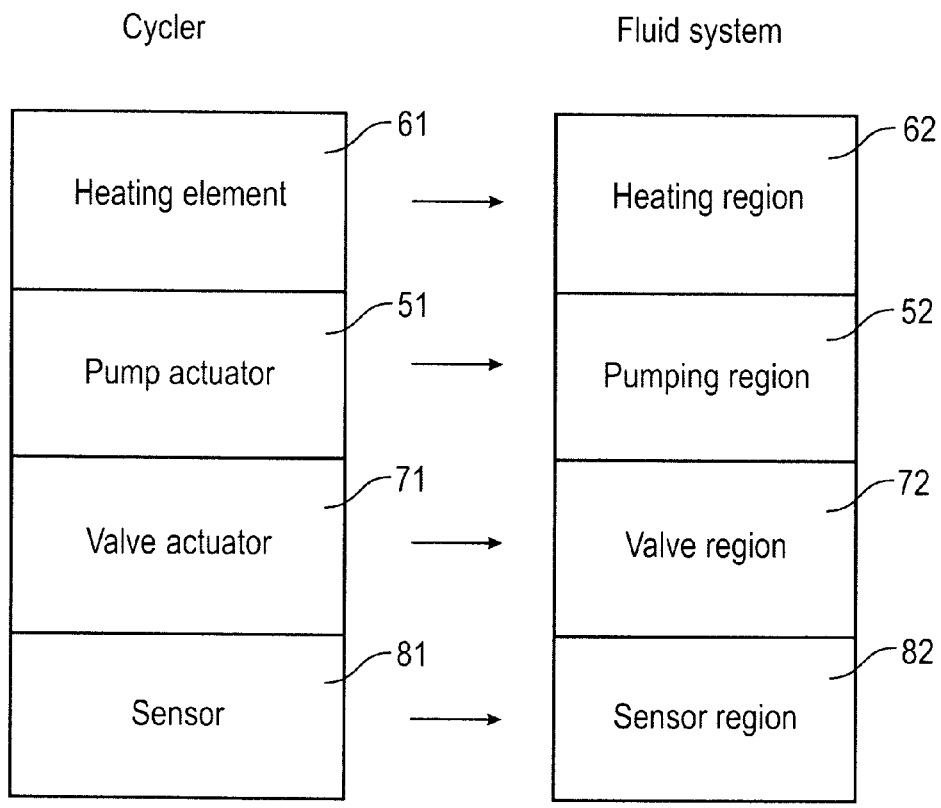
FIG. 3 a schematic diagram of the division of the peritoneal dialysis system into a dialysis machine and a fluid system.

In order nevertheless to enable a control of the peritoneal dialysis by the dialysis machine 40, the fluid system has to be coupled to the dialysis machine 40. In this respect, it is shown schematically in FIG. 3 how individual elements of the dialysis machine 40 are coupled to corresponding regions of the fluid system.

The dialysis machine 40 in this respect has a heating element 61. This must be coupled to a corresponding heating region 62 of the fluid system. The coupling in this respect enables the transfer of thermal energy from the heating element 61 to the dialysate present in the heating region 62.

The dialysis machine 40 furthermore has one or more pump actuators 51 which are coupled to a pump region 52 of the fluid system. The pump actuators 51 in this respect generate a pump force which is transferred to the pump region 52. The liquid present in the pump region 52 can hereby be moved along the fluid paths.

The dialysis machine furthermore has one or more valve actuators 71. They generate a closing movement which is transferred to corresponding valve regions 72 of the fluid paths. The valve regions 72 of the fluid paths can hereby be correspondingly closed or opened.

The dialysis machine furthermore has one or more sensors 81. They are coupled to a corresponding sensor region 82 of the fluid system. The sensors 81 can hereby measure specific properties of the dialysate. The temperature of the dialysate can in particular be measured hereby. Provision can furthermore be made that the pressure in the fluid system is determined.

The dialysis machine naturally optionally has further actuators and/or sensors which do not have to be coupled to the fluid paths.

The individual components of a peritoneal dialysis system should now be presented in more detail in the following with reference to embodiments.

1. Fluid System 1.1 Dialysis Container

Fresh dialysate is usually provided in plastic bags. Such plastic bags usually have two layers of plastic film which are welded to one another in a marginal region and thus form a container which is filled with fresh dialysate. A hose element is usually welded to this container by which the dialysate can be removed from the bag. A connector is usually arranged at the hose element via which the dialysate container can be connected to the other fluid paths. The bag furthermore usually has a cut-out or eyelet at the side disposed opposite the hose and the bag can be hung onto a hook by it. It can hereby be ensured that the dialysate flows out of the bag without problem.

The dialysate usually comprises a buffer, an osmotic agent and electrolytes. Bicarbonate can e.g. be used as the buffer in this respect. Glucose is usually used as the osmotic agent. Alternatively, glucose polymers or glucose polymer derivatives can also be used. The electrolytes usually include calcium and sodium.

The dialysate can be heat sterilized in this respect. This advantageously takes place after the dialysate has been filled into the bag. Both the dialysate and the bag are hereby heat sterilized. In this respect, the filled bag is usually first packed into an outer packaging, whereupon the total system is sterilized.

Since the finished dialysate solution can often not be heat sterilized or cannot be stored for a long time in dependence on the ingredients, provision can be made to store individual components of the dialysate separately and only to combine them shortly before the treatment. A first individual solution in this respect usually includes the buffer, while a second individual solution includes glucose and electrolytes. Optionally, more than two individual solutions, and thus more than two regions, can also be provided in a bag. In this respect, a multi-chamber bag, in particular a double-chamber bag, can be provided which has a plurality of separate regions for the storage of the individual solutions. These regions are separated by a connection element which can be opened mechanically to mix the individual solutions with one another. A so-called peel seam can in particular be provided between the two regions of the bag in this respect and opens on the application of a specific pressure to at least one of the regions of the bag.

Since relatively large quantities of dialysate are consumed during a night-time peritoneal dialysis treatment, a plurality of dialysate containers are usually used in parallel. They are connected to the fluid paths via corresponding connectors and can be used for the filling of the patient by a corresponding connection of the valves.

1.2 Outflow

For the disposal of the consumed dialysis fluid, it can either be led off immediately into the drainage system or first be collected in an outflow container. A bag is usually likewise used as an outflow container in this respect. It is empty before the start of the treatment and can thus take up the consumed dialysate. The bag can then be correspondingly disposed of after the end of the treatment.

1.3 Cassette

As already initially described, the fluid system has a plurality of regions in which the dialysis machine has to have an effect on the fluid system. The fluid system has to be coupled to the dialysis machine for this purpose.

Cassettes are used to simplify the coupling of the fluid paths to the dialysis machine and the effect of the corresponding elements of the dialysis machine on the fluid paths. A plurality of regions in which the dialysis machine has an effect on the fluid paths are jointly arranged in such a cassette. For this purpose, a cassette usually has a hard part of plastic into which chambers open to one side are introduced as fluid paths. These chambers are covered by a flexible plastic film which provides the coupling to the dialysis machine. The flexible plastic film is in this respect usually welded to the hard part in a marginal region. The cassette is pressed with a coupling surface of the dialysis machine so that the actuators and/or sensors of the dialysis machine come into contact with corresponding regions of the cassette.

The cassette furthermore has connections for the connection of the dialysate container 10, of the connector 30 as well as of the outflow 20.

A cassette in this respect usually includes at least one pump region and one or more valve regions. The liquid transport can thus be controlled by the fluid system via the cassette. The cassette can furthermore have sensor regions which enable a simple coupling of sensors of the dialysis machine to the fluid system. The cassette can optionally furthermore have one or more heating regions which can be coupled to corresponding heating elements of the dialysis machine.

Figure 4A:
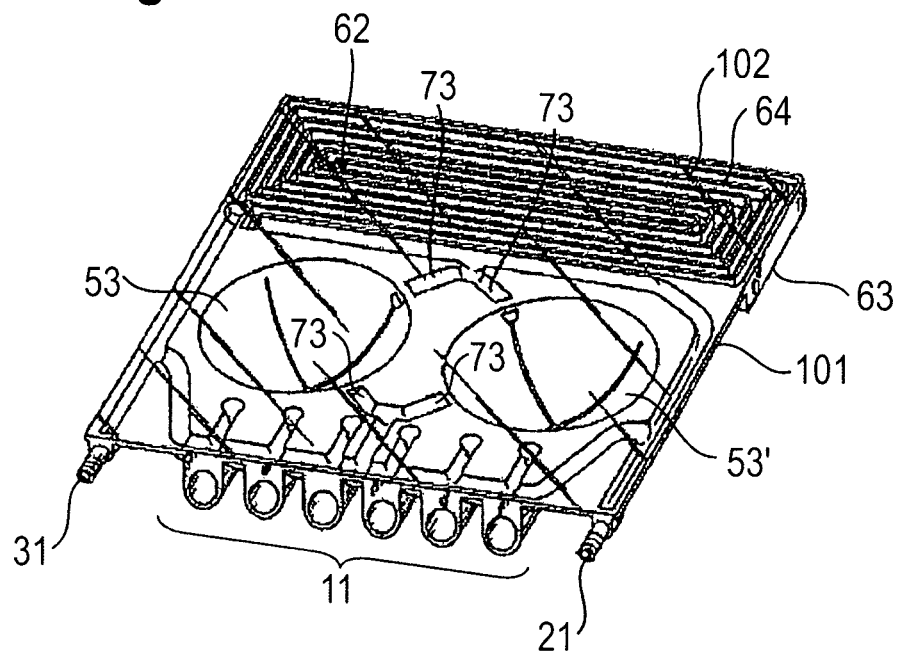
FIG. 4 a first embodiment of a cassette.
Figure 4B:
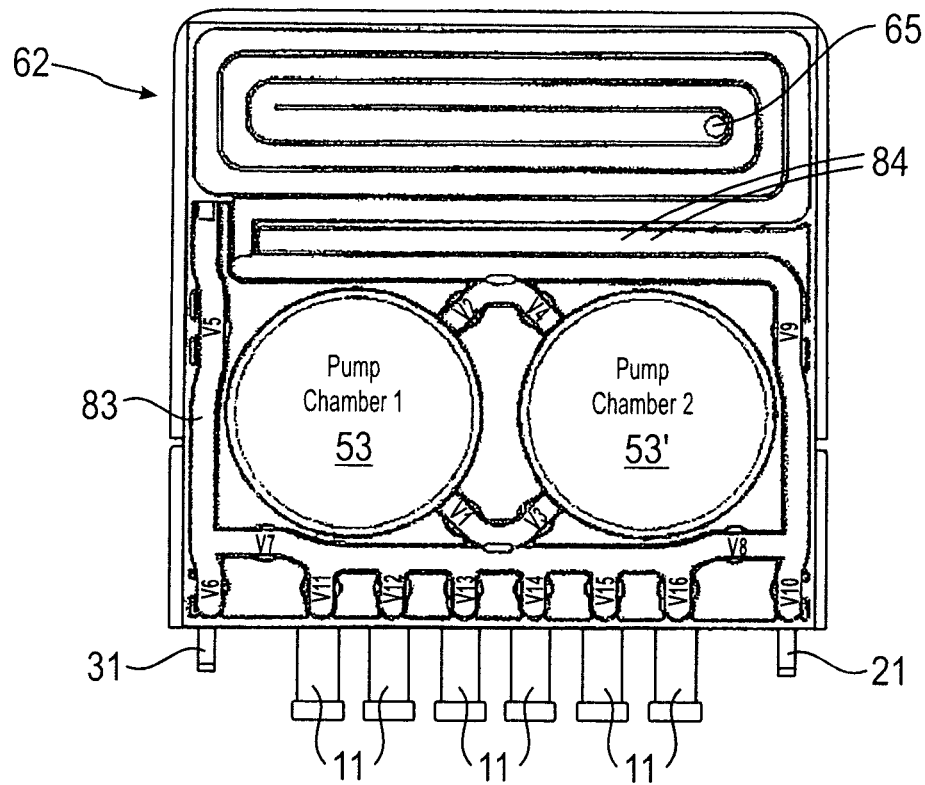

A first embodiment of a cassette is shown in FIGS. 4a and 4b. It has a hard part 101 of plastic in which the fluid paths and coupling regions are introduced as corresponding cut-outs, chambers and passages. The hard part can in this respect be produced e.g. as an injection molded part or as deep drawn part. The coupling plane of the hard part 101 is covered by a flexible film 102 which is welded to the hard part in a marginal region. The flexible film 102 is pressed with the hard part by the pressing of the cassette with a coupling surface of the dialysis machine. The fluid paths within the cassette are separated from one another in a fluid tight manner by the pressing of the flexible film with the web regions of the hard part.

The cassette has connections for the connection of the cassette to the other fluid paths. On the one hand, a connection 21 is provided for the connection to the outflow 20 as well as a connection 31 for the connection to the connector 30. Corresponding hose elements which are not shown in FIG. 4a can be provided at these connections. The cassette furthermore has a plurality of connections 11 for the connection of dialysate containers 10. The connections 11 are in this respect designed in the first embodiment as connectors to which corresponding connector elements can be connected.

The connections are in each case in connection with fluid paths within the cassette. Valve regions are provided in these fluid paths. In these valve regions, the flexible film 102 can be pressed into the hard part 101 via valve actuators at the machine side such that the corresponding fluid path is blocked. The cassette in this respect first has a corresponding valve for each connection via which this connection can be opened or closed. The valve V10 is in this respect associated with the connection 21 for the outflow 20; the valve V6 is associated with the connection 31 for the patient connector 30. The valves V11 to V16 are associated with the connections 11 for the dialysate container 10.

Pump chambers 53 and 53' are furthermore provided in the cassette via which corresponding pump actuators of the dialysis machine can be actuated. The pump chambers 53 and 53' are in this respect concave cut-outs in the hard part 101 which are covered by the flexible film 102. The film can now be pressed into the pump chambers 53 and 53' or pulled out of these pump chambers again by pump actuators of the dialysis machine. A pump flow through the cassette can hereby be generated in cooperation with the valves V1 to V4 which connect the accesses and outflows of the pump chambers 53 and 53' and are designated by the reference numeral 73 in FIG. 4a. The pump chambers can in this respect be connected via corresponding valve circuits to all connections of the cassette.

A heating region 62 is furthermore integrated into the cassette. In this region, the cassette is brought into contact with heating elements of the dialysis machine which heat the dialysate flowing through this region of the cassette. The heating region 62 in this respect has a passage for the dialysate which extends spirally over the heating region 62. The passage is in this respect formed by webs 64 of the hard part which are covered by the flexible film 102.

The heating region 62 is in this respect provided at both sides of the cassette. A flexible film is also arranged at the hard part in the heating region at the lower side 63 of the cassette for this purpose. The flexible film is in this respect also welded to the hard part in a marginal region. A passage is likewise arranged at the lower side and the dialysate flows through it. The passages on the lower side and on the upper side are in this respect formed by a middle plate of the hard part which separates the upper side from the lower side and on which webs are downwardly and upwardly provided which form the passage walls. In this respect, the dialysate first flows spirally on the upper side up to the aperture 65 through the middle plate from where the dialysate flows back at the lower side through the corresponding passage. The heating surface which is available for the heating of the fluid can be correspondingly enlarged by the heating region provided at the upper side and at the lower side. An embodiment of the cassette is, however, naturally also possible in which a heating region is only arranged on one side of the cassette.

Embodiments of the cassette are furthermore possible in which a heating element is integrated into the cassette. An electrical heating element such as a heating coil can in this respect in particular be cast into the hard part of the cassette. A heating element on the machine side can thus be dispensed with and the throughflow heating can be integrated into the cassette. In this respect, electrical contacts are arranged at the cassette for the connection of the electrical heating element.

The cassette furthermore has sensor regions 83 and 84 by which temperature sensors of the dialysis machine can be coupled to the cassette. The temperature sensors in this respect lie on the flexible film 102 and can thus measure the temperature of the liquid flowing through the passage disposed below. Two temperature sensors 84 are in this respect arranged at the inlet of the heating region. A temperature sensor 83 via which the temperature of the dialysate pumped to the patient can be measured is provided at the outlet at the patient side.

Figure 5:
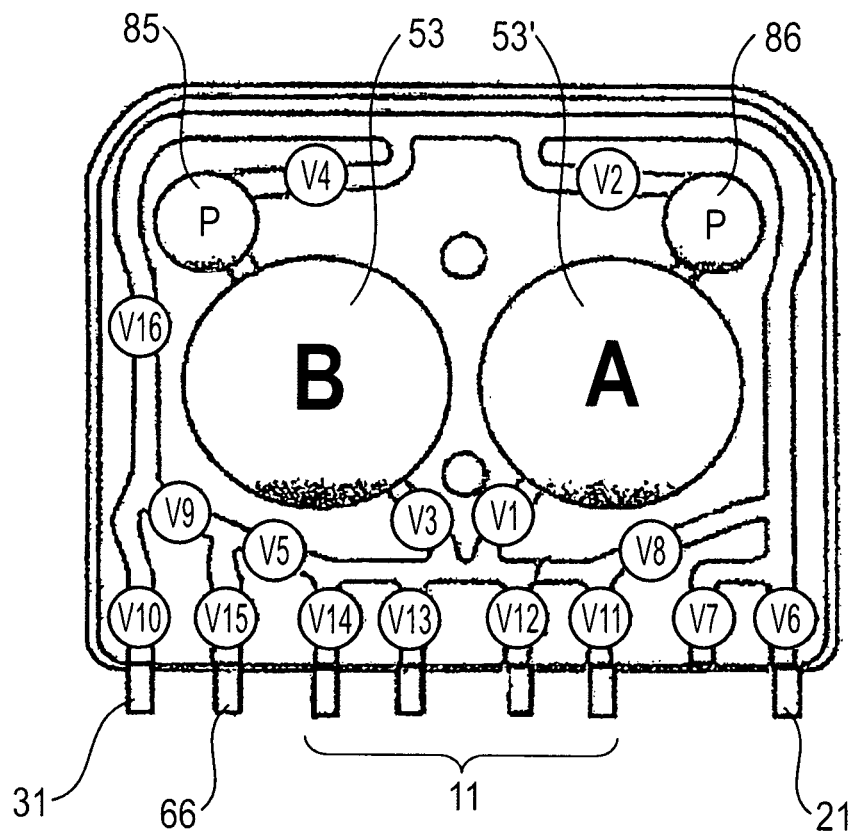
FIG. 5 a second embodiment of a cassette.

A second embodiment for a cassette is shown in FIG. 5. The cassette in this respect substantially corresponds in its design to the first embodiment, but does not include any heating region. On the use of this cassette, the heating therefore does not take place as shown in the first embodiment via a heating region integrated into the cassette, but rather e.g. via a heating bag which is placed onto a heating plate of the dialysis machine.

The second embodiment of a cassette shown in FIG. 5 in turn has fluid paths which can be opened and closed via valve regions which are here likewise numbered consecutively from V1 to V16. The cassette furthermore has connections for the connection to further components of the fluid system. In this respect, the connection 21 is in turn provided for the connection to the outflow 20 and the connection 31 for connection to the connector 30 to the patient. Connections 11 are furthermore provided for the connection of dialysate containers 10.

Unlike the first embodiment, the cassette shown in the second embodiment has a further connection 66 for the connection of a heating bag. In this respect, the liquid can be pumped into a heating bag via the connection 66 for the heating of the fluid from the dialysate containers 10. This heating bag lies on a heating element so that the fluid present in the heating bag can be heated. The fluid is thereupon pumped from the heating bag to the patient.

The pump chambers 53 and 53' and the valves V1 to V4 correspond in design and function to the corresponding components in the first embodiment.

Unlike the first embodiment, the cassette in the second embodiment does not have any sensor region for the connection of a temperature sensor. It is rather arranged in the region of the heating elements. The cassette, however, has measurement regions 85 and 86 for the measurement of the pressure in the pump chambers 53 and 53'. The measurement regions 85 and 86 are in this respect chambers which are in fluid communication with the pump chambers and are likewise covered by the flexible film. Pressure sensors at the apparatus side which measure the pressure in the measurement chambers 85 and 86 and thus in the pump chambers 53 and 53' can be coupled to the measurement regions.

The connection of the connections 11, 21, 31 and 66 of the cassette to the further components of the fluid system takes place via hose connections in the second embodiment. Connectors are optionally arranged at these hose connections.

1.3 Hoses

The connection between the individual containers of the system, the cassette and the patient connector usually takes place via hose connections. Since they are in each case disposable articles, the hoses are in this respect usually already fixedly connected at least one side to a further element. Hoses can e.g. already be provided at one or more of the connections of the cassette. Hoses can likewise already be in fixed communication with bags.

1.4 Connections

The fluid system is usually divided into a plurality of parts and packaged in sterile form in each case. These parts first have to be connected to one another for the treatment. The cassette and the dialysate bag or bags are in this respect in particular packaged separately from one another.

The connections between the individual elements of the fluid system usually takes place via connectors. The connectors are in this case designed so that they enable a sterile connection between the individual components. This takes place e.g. via corresponding protective films which are automatically opened on the closing of the connector.

The connection of the individual components can in this respect take place manually by an operator or by the patient him or herself. Provision can alternatively be made that the connection of the individual components takes place by the dialysis machine.

For this purpose, the corresponding connectors can e.g. be placed into a connector receiver of the dialysis machine and can be automatically joined together by the dialysis machine.

An electronic control can furthermore be provided which monitors that the correct components of the system are connected to one another. Identification means such as barcodes or RFIDs which identify the components can be provided at the connectors for this purpose. The dialysis machine in this respect includes an identification means detection unit such as a barcode reader or an RFID detection unit which detects the identification means on the connectors. The controller of the peritoneal dialysis can hereby recognize whether the correct connectors were inserted.

Such a check of the correct assembly of the fluid system can in this respect in particular be combined with an automatic connection of the connectors. The system thus first checks whether the correct connectors were placed into the connector receivers. The connection between the connectors is only established by the dialysis machine when the correct connectors were inserted. Otherwise, the dialysis machine draws the attention of the user to the fact that the wrong connectors have been inserted.

2. The Dialysis Machine

The individual components of a dialysis machine should now be described in more detail in the following with reference to two embodiments.

Figure 6:
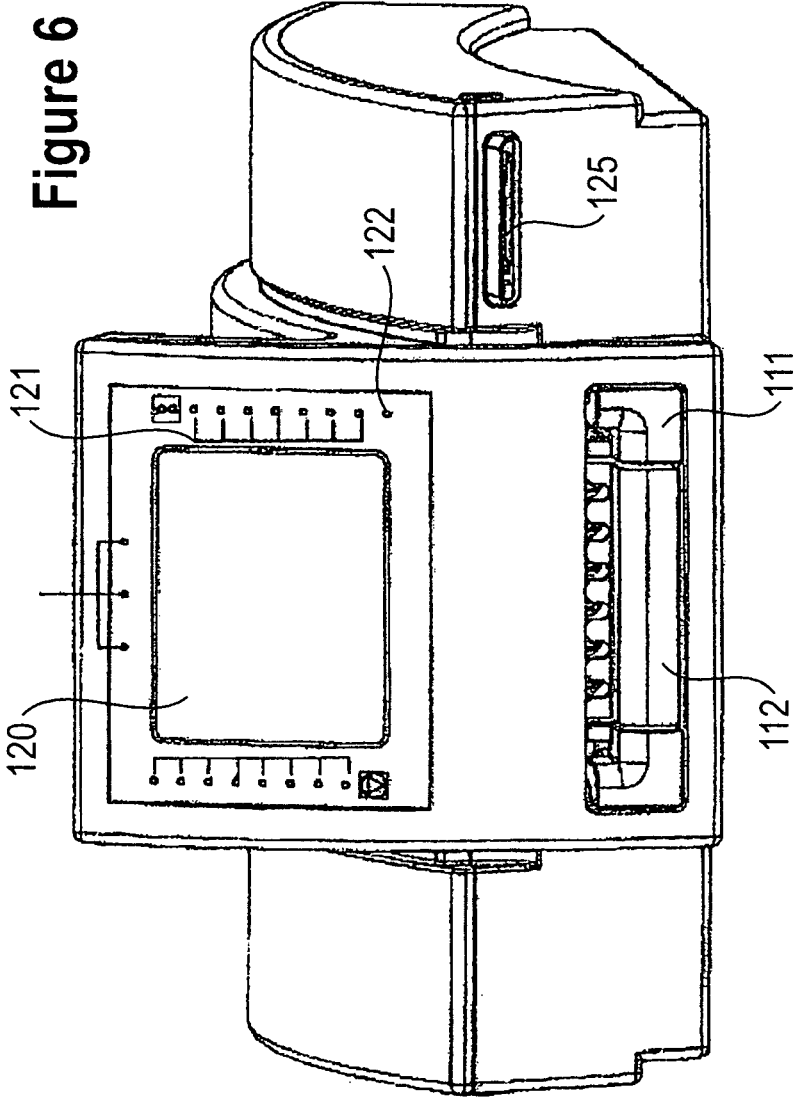
FIG. 6 a perspective view of a first embodiment of a dialysis machine.
Figure 7:
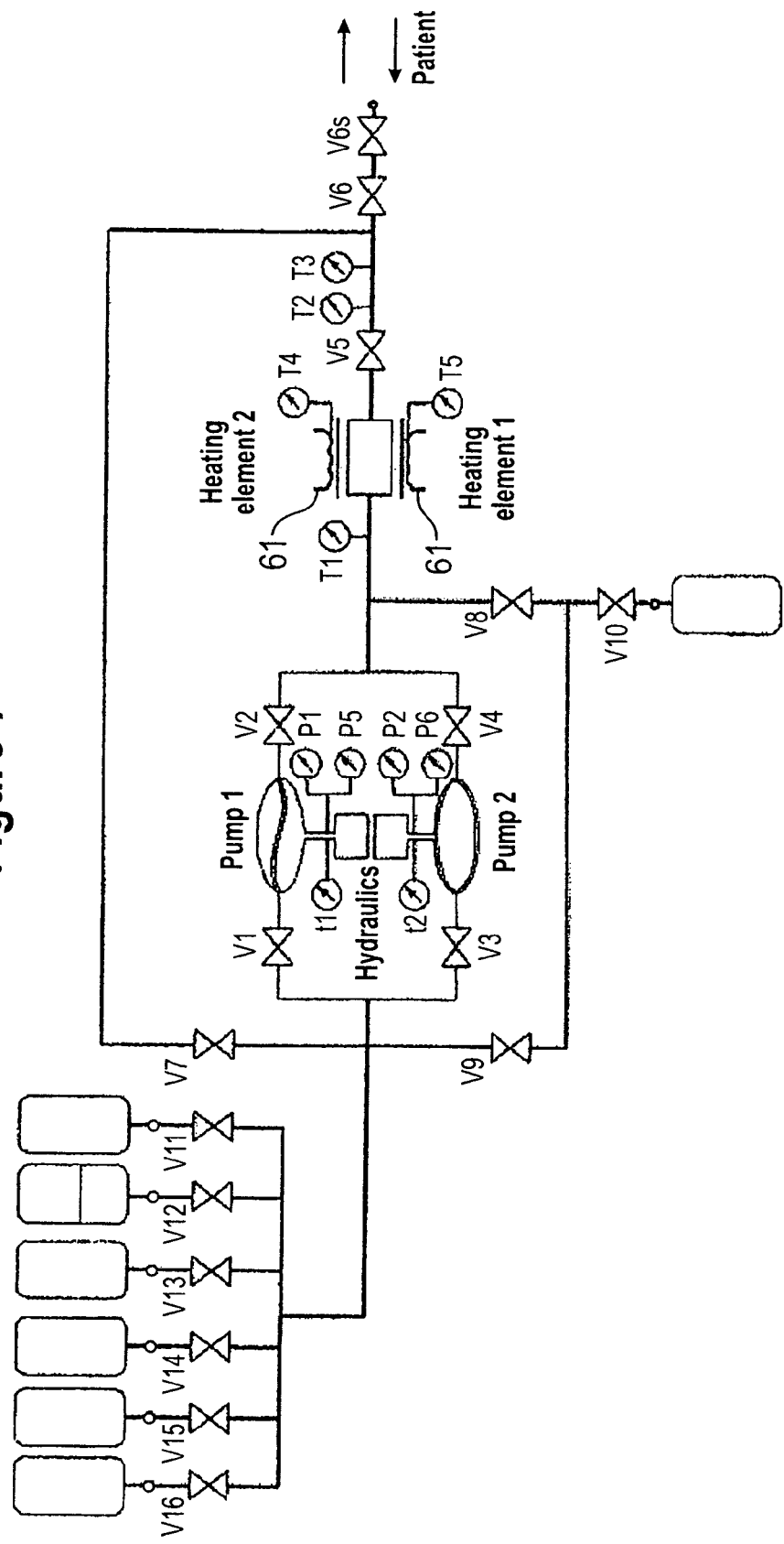
FIG. 7 a flowchart of a first embodiment of a peritoneal dialysis system.

A first embodiment of a dialysis machine is shown in this respect in FIG. 6 in which the first embodiment of a cassette is used. The peritoneal dialysis system resulting from the first embodiment of a dialysis machine and the first embodiment of a cassette is shown in FIG. 7 in this respect.

Figure 8:
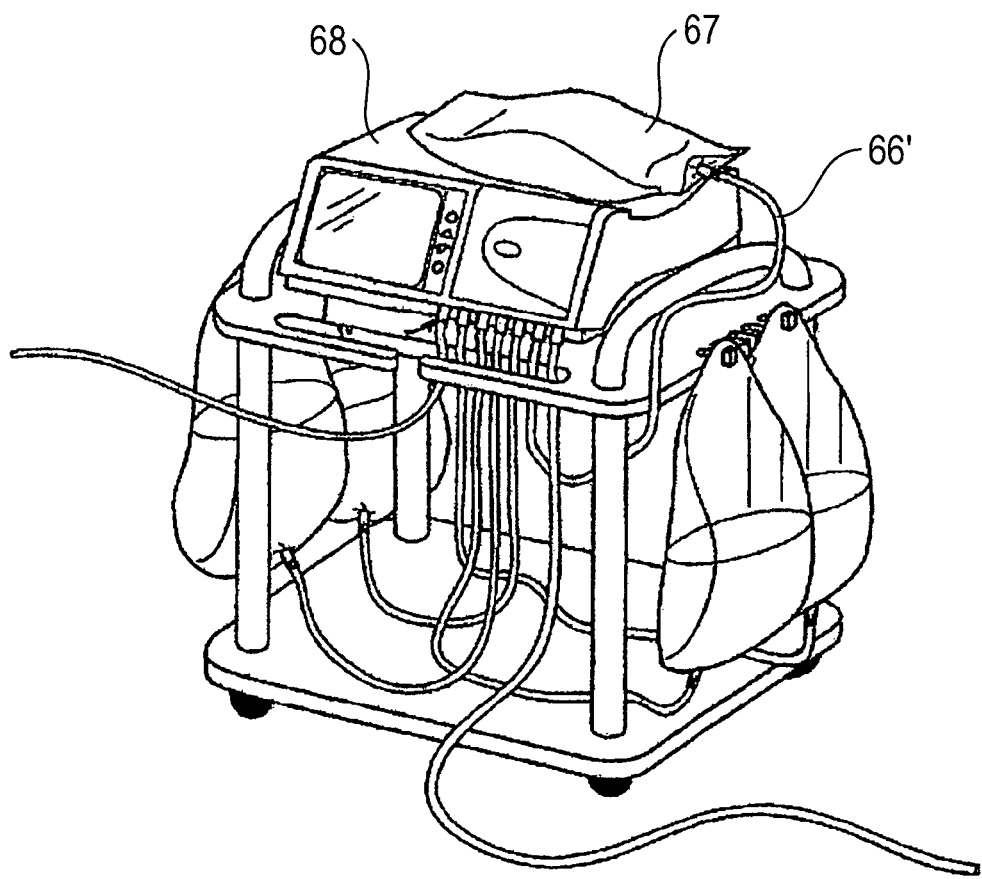
FIG. 8 a perspective view of a second embodiment of a dialysis machine.

A second embodiment of a dialysis machine is shown in FIG. 8 in which the second embodiment of a cassette is used.

Figure 9:
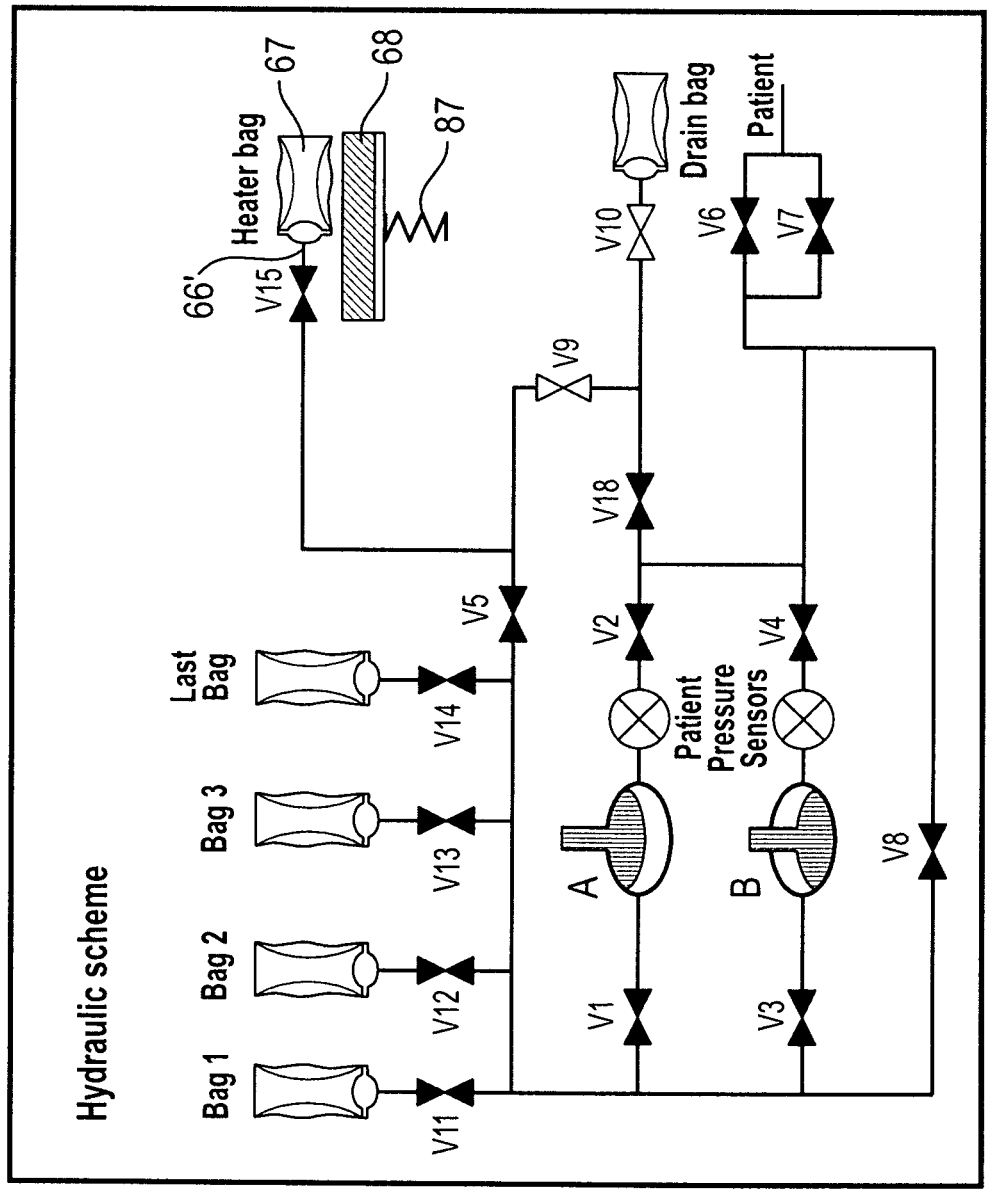
FIG. 9 a flowchart of a second embodiment of a peritoneal dialysis system.

The dialysis system resulting from the combination of the second embodiment of a dialysis machine and of the second embodiment of a cassette is then shown in FIG. 9.

The two embodiments differ in this respect, on the one hand, in the design of the heating, in the coupling between the dialysis machine and the cassette and in the design of the actuators and sensors.

2.1 Heating

The fresh dialysate has to be brought to body temperature before it is conveyed into the abdomen of the patient. The dialysis machine has a corresponding heating for this purpose.

The heating in this respect usually takes place via one or more heating elements. The heating elements can in this respect e.g. be ceramic heating elements. With such ceramic heating elements, a resistance strip is applied to a ceramic carrier. The heating strip is heated by the application of a voltage to it, whereby the ceramic carrier material is also heated. The ceramic heating element is in this respect usually arranged on a heating plate. It can be made of aluminum, for example. The fluid paths are in turn coupled to the heating plate so that the dialysate present in the fluid paths can be heated.

Two different designs are available for the heating of the fluid. On the one hand, a larger quantity of dialysate can first be heated which is only pumped to the patient after the heating phase. This usually takes place via a heating bag which is placed on a heating plate of the dialyzer.

The heating bag can in this respect be the dialysis bag in which the dialysate is provided. Usually, however, a separate heating bag is used in which the dialysate is pumped for heating. If the dialysate is heated in the heating bag, it is pumped to the patient from there.

Such a concept is realized in the second embodiment of a dialysis machine shown in FIGS. 8 and 9. In this respect, a heating bag 67 is provided which lies on a heating plate 68. The heating plate 68 is in this respect arranged on the upper side of the peritoneal dialyzer so that it is easily accessible. The heating bag 67 is in this respect connected to the cassette via a line 66'. The cassette in this respect has the valves V5, V9 and V15 via which the heating bag 67 can be connected to the other components of the fluid system. Fresh dialysate can thus be pumped from the dialysate containers 10 via the pump chambers to the heating bag 67. At the start of a treatment, the heating bag 67 is therefore first filled with cold dialysate. The dialysate in the heating bag 67 is then heated to body temperature via the heating plate 68. The dialysate is thereupon pumped to the patient via the pump chambers. The heating bag 67 can thereupon be filled again so that the dialysate quantity required for the next treatment cycle can be heated.

A temperature sensor 88, which is in contact with the heating bag 67 and can thus measure the temperature of the dialysate in the heating bag 67, is advantageously provided in the region of the heating plate 68 in this respect. A temperature sensor can furthermore be provided at the heating plate or at the heating element which measures the temperature of the heating element or of the heating plate. A corresponding controller now makes sure that the heating plate does not become too hot for the material of the bag.

The heating bag 67 can additionally take over functions in the balancing of the fluid flows. The heating plate 68 can thus be part of scales 87 via which the weight of the heating bag 67 can be determined. The fluid quantity which is supplied to the patient after heating can hereby be determined.

Alternatively to the heating of the dialysate via a heating bag shown in the second embodiment, the dialysate can also be heated while it is being pumped to the patient. The heating thus works in the form of a continuous-flow water heater which heats the dialysate moved through the fluid system while it is being pumped through the fluid paths.

In this concept, a dialysate passage is provided which is coupled to a heating element of the dialysis machine. While the dialysate flows through the dialysate passage, it takes up heat from the heating element of the dialysis machine while so doing.

Such a concept is implemented in the first embodiment of a dialysis machine which is shown in FIGS. 6 and 7. The heating region is integrated in the cassette in this respect, as was already shown above. On the coupling of the cassette to the dialysis machine, the heating region of the cassette comes thermally into contact with heating elements of the dialysis machine.

The heating elements can in this respect likewise be designed as ceramic heating elements and can be in contact with heating plates which are the coupled to the heating region of the cassette. As already shown with respect to the cassette, a respective heating plate which heats the dialysate flowing through the heating region is in this respect in contact both with the upper side and with the lower side of the heating region.

Respective temperature sensor regions are provided in the cassette at the inflow and at the outflow of the heating region and come into contact with temperature sensors of the peritoneal dialysate by the coupling of the cassette. The temperature of the dialysate flowing into the heating region and the temperature of the dialysate flowing out of the heating region can thus be determined by the temperature sensors T1 to T3. Temperature sensors T4 and T5 are furthermore provided which determine the temperature of the heating elements and/or of the heating plates.

The use of at least two heating elements in this respect makes it possible to connect the heating elements to one another in each case such that they output substantially the same power at a supply voltage of 220 V as with a supply voltage of 110 V. For this purpose, the two heating elements are operated in a parallel circuit at 110 V, whereas they are operated in a series circuit at a supply voltage of 220 V. Such an adaptation of the connection of the heating elements to the supply voltage can in this respect be implemented independently of whether the heating takes place in accordance with the first or the second embodiment.

2.2 Coupling the Cassette

To enable a coupling of the actuators and/or sensors of the dialysis machine to the corresponding regions of the cassette, the dialysis machine has a cassette receiver with a coupling surface to which the cassette can be coupled. The corresponding actuators, sensors and/or heating elements of the dialysis machine are arranged at the coupling surface. The cassette is pressed with this coupling surface such that the corresponding actuators, sensors and/or heating elements come into contact with the corresponding regions in the cassette.

In this respect, a mat of a flexible material, in particular s silicone mat, is advantageously provided at the coupling surface of the dialysis machine. It ensures that the flexible film of the cassette is pressed with the web regions of the cassette and thus separates the fluid paths within the cassette.

A peripheral margin of the coupling surface is furthermore advantageously provided which is pressed with the marginal region of the cassette. The pressing in this respect advantageously takes place in an airtight manner so that an underpressure can be built up between the coupling surface and the cassette.

A vacuum system can optionally also be provided which can pump air out of the space between the coupling surface and the cassette. A particularly good coupling of the actuators, sensors and/or heating elements of the peritoneal dialysis device with the corresponding regions of the cassette is hereby made possible. In addition, the vacuum system allows a leak tightness check of the cassette. A corresponding vacuum is applied after the coupling for this purpose and a check is made whether this vacuum is maintained.

The pressing on of the cassette takes place pneumatically, for example. For this purpose, usually an air cushion is provided which is filled with compressed air and thus presses the cassette onto the coupling surface.

The cassette receiver usually has a receiver surface which is disposed opposite the coupling surface and into which the hard part of the cassette is inserted. The receiver surface advantageously has corresponding recesses for this purpose. The receiver surface with the inserted cassette can then be pressed onto the coupling surface via a pneumatic pressing apparatus.

The insertion of the cassette can in this respect take place in different manner. In the first embodiment of a dialysis machine which is shown in FIG. 6, a drawer 11 is provided for this purpose which can be moved out of the dialysis machine. The cassette is inserted into this drawer. The cassette is then pushed into the dialysis machine together with the drawer. The pressing of the cassette with the coupling surface which is arranged in the interior of the apparatus thereupon takes place. In this respect, the cassette and the coupling surface are first moved mechanically toward one another and then pressed with one another pneumatically.

Figure 10:
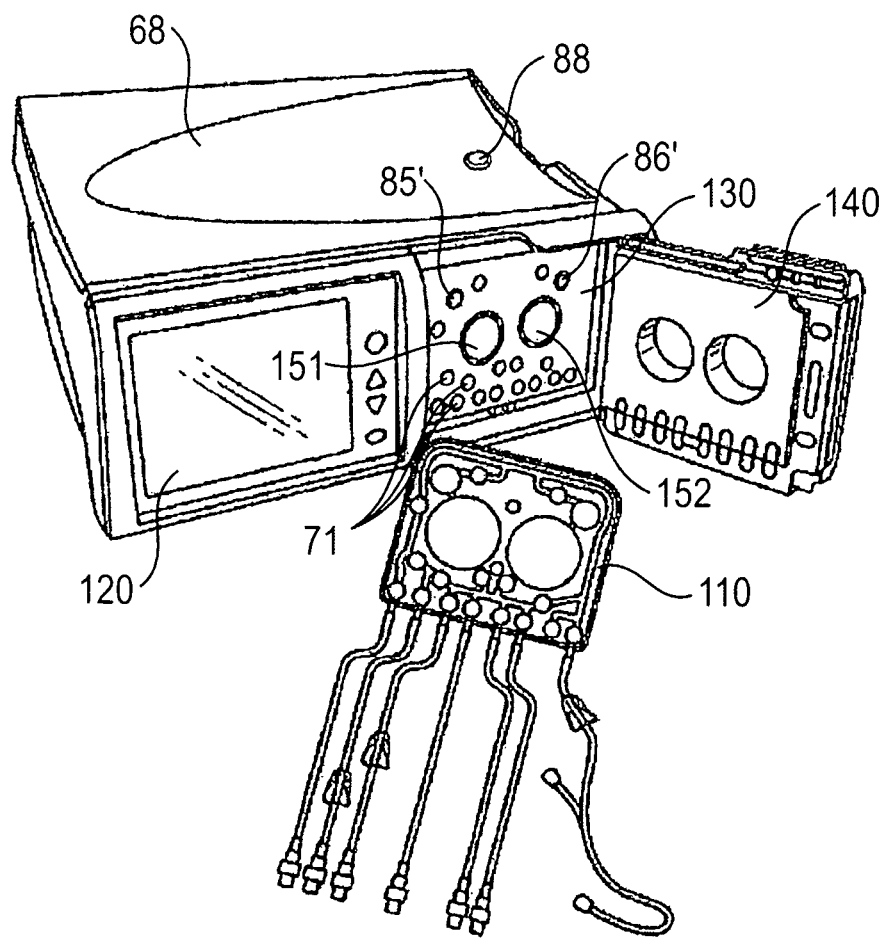
FIG. 10. the coupling of the cassette in the second embodiment of a peritoneal dialysis system.

The coupling of a cassette 110 in accordance with the second embodiment is shown in more detail in FIG. 10. The coupling surface 130 is freely accessible by opening a door 140 so that the cassette can be arranged at the correct position at the coupling surface 130. The coupling surface 130 is in this respect inclined rearwardly toward the vertical, which enables an easier coupling. The door 140 can now be closed so that a receiver surface at the door comes into contact with the rear side of the cassette. The pressing now takes place by an air cushion arranged at the door. In addition, a vacuum is applied between the coupling surface and the cassette 110.

The first embodiment of a dialysis machine furthermore has an apparatus for automatic connecting. A connector receiver 112 is provided for this purpose into which the connectors of the dialysate bag 10 are inserted. The connector receiver 112 then moves into the apparatus where a barcode reader is provided which reads the barcodes applied to the connectors. The apparatus can thus check whether the correct bags were inserted. If the correct bags are recognized, the connector receiver 112 moves in completely and so connects the connectors of the bag to the connections 11 of the cassette made as connectors.

In the second embodiment, such an automatic connecting was, in contrast, dispensed with. Hose sections are therefore arranged at the connections 11 of the cassette and have to be manually connected to the corresponding bags via connectors.

2.3 Pump Actuators

The pumping of the liquid through the fluid system takes place in the embodiments by a membrane pump which is formed by the pump chambers 53 and 53' together with the flexible film of the cassette. If the flexible film is in this respect pressed into the pump chamber by a corresponding pump actuator, fluid is pumped out of the pump chamber into the opened regions of the fluid paths of the cassette. Conversely, fluid is sucked out of the fluid paths into the pump chamber by pulling the film out of the pump chamber.

The pump stroke in this respect takes place by movement of a pump actuator into the pump chamber. The pump actuator is moved away from the pump chamber again for the suction stroke. An underpressure arises in this respect due to the airtight pressing of cassette and coupling surface by which the flexible film of the cassette follows the pump actuator and is thus pulled out of the pump chamber again.

To enable a good coupling of the pump actuator to the flexible film of the cassette, a vacuum system can moreover be provided. In this respect, in particular the force with which the flexible film is moved away from the pump chamber at a maximum during a suction stroke can be set via the setting of a corresponding vacuum between the coupling surface and the cassette.

The suction force of the pump can hereby be set very finely. The pump force is in contrast set by the thrust force of the actuator.

The balancing of the fluid flows can in this respect take place by the counting of the suction and pump strokes since the membrane pump has a high precision of the fluid quantity pumped with each stroke.

2.3.1. Hydraulic Drive

Figure 11:
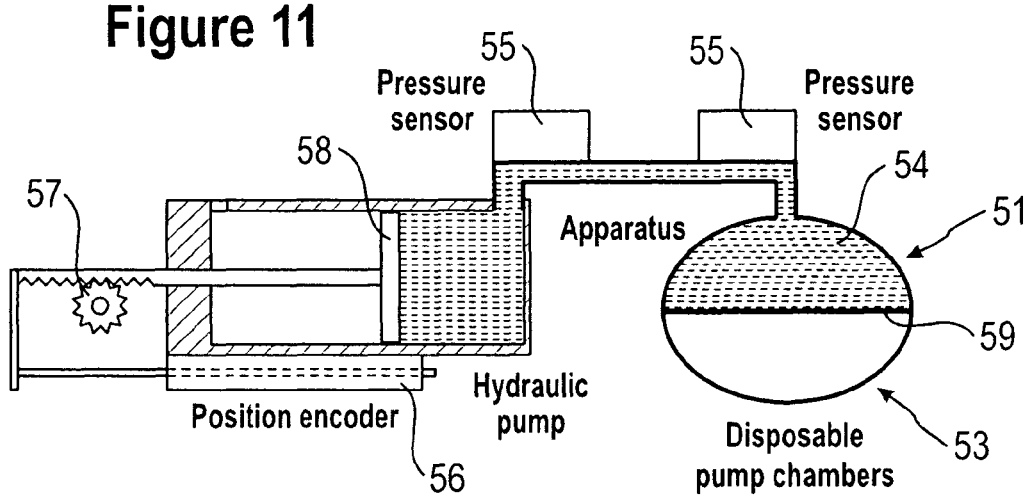
FIG. 11 a first embodiment of a pump actuator.

The structure of a first embodiment of a pump actuator is shown in FIG. 11. The pump actuator is moved hydraulically in this respect. A membrane 59 is provided for this purpose which is placed at the flexible film of the cassette. The membrane 59 can in this respect be produced e.g. from silicone. A chamber 54 which can be filled with hydraulic fluid is provided behind the membrane 59. By application of an overpressure in the chamber 54, the membrane 59, and with it the flexible film, is pressed into the pump chamber 53 of the cassette. By application of an underpressure to the chamber 54, the membrane 59 is, in contrast, pulled into the chamber 54. Due to the underpressure between the flexible film and the membrane, the flexible film follows this movement so that the volume of the pump chamber 53 increases. The pump process with the pump stroke and the suction stroke is shown schematically in FIG. 12*b* in this respect.

A hydraulic pump 58 is provided for the operation of the pump hydraulic. It has a cylinder in which a piston can be moved to and fro via a motor 57. The hydraulic fluid is hereby pressed into the chamber 54 or sucked out of it again via a corresponding connection line. A position encoder 56 is provided at the hydraulic pump 58 in this respect and the movement of the piston can be recorded via it. It can hereby be determined how much hydraulic fluid was pressed into the chamber 54 and how much hydraulic fluid was removed from it. Pressure sensors 55 are furthermore provided at the hydraulic system which measure the pressure in the hydraulic system. They on the one hand allow a functional check of the hydraulic system since the data of the pressure sensors can be compared with those of the position encoder 56 and the leak tightness of the hydraulic system can hereby be checked.

In addition, the pressure sensors allow a determination of the pressure in the pump chamber 53 of the cassette. If the hydraulic pump 58 is not moved, a pressure balance is adopted between the chamber 54 and the pump chamber 53. The pressure of the hydraulic fluid thus corresponds to the pressure in the pump chamber 53.

Figure 12A:
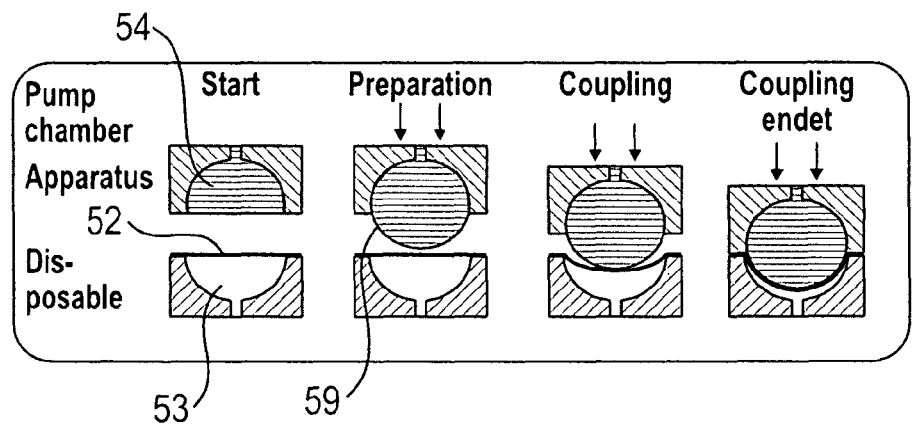
FIG. 12 the coupling of a pumping region of the cassette to a pump actuator.

The coupling procedure of the pump actuator to the pump chamber 53 is now shown in FIG. 12*a*. In this respect, the chamber 54 is first loaded with hydraulic fluid such that the membrane 59 arches outwardly for the preparation of the coupling. The coupling surface and the cassette are thereupon moved toward one another so that the membrane 59 presses the flexible film of the cassette into the pump chamber 53.

Figure 12B:
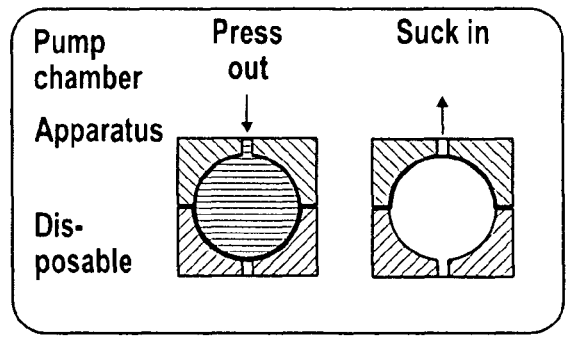

After the pressing of the coupling surface and of the cassette, the space between the membrane and the flexible film is outwardly closed in an airtight manner so that the flexible film follows the movement of the membrane. This is shown in FIG. 12*b*.

The pump actuator shown in FIG. 11 is in this respect implemented in the first embodiment of a dialysis machine, as can also be seen from FIG. 7. In this respect, a corresponding pump actuator is respectively provided for each of the two pump chambers 53 and 53'.

2.3.2 Electromechanical Drive

Alternatively, the pump actuator can also be operated in an electric motor manner. A correspondingly shaped ram is provided for this purpose which is pressed toward or away from the flexible film via an electric motor, in particular via a stepped motor, and the pump stroke or suction stroke is thus generated. Such pump actuators 151 and 152 are shown in the embodiment in FIG. 10. A vacuum system is in this respect advantageously provided which ensures that the flexible film also follows the ram in the suction movement.

2.4 Valve Actuators

A valve plunger can be provided as the valve actuator which presses the flexible film of the cassette into a corresponding chamber of the hard part and so closes the fluid passage in this region. The valve actuator can in this respect e.g. be pneumatically actuated. The plunger can in this respect be biased via a spring so that it either opens without pressure or closes without pressure.

Alternatively, the valve actuator can be implemented via a flexible membrane which is moved hydraulically or pneumatically. The flexible membrane is in this respect moved toward the cassette by application of pressure and so presses a corresponding valve region of the flexible film into a fluid passage to close it.

Valve actuators 1, which are coupled to the valve regions V1 to V16 of the cassette, can be recognized on the coupling surface in FIG. 10.

2.5 Sensors

The dialysis machine has sensors via which the machine can be controlled or its proper functioning can be monitored.

On the one hand, in this respect, one or more temperature sensors are provided via which the temperature of the dialysate and/or of the heating elements can be measured. In the first embodiment, the temperature sensors are in this respect arranged at the coupling surface to the cassette and can so measure the temperature of the dialysate flowing through the cassette. In the second embodiment, in contrast, a temperature sensor 88 is provided on the heating plate 68 which measures the temperature of the dialysate present in the bag 67. Temperature sensors can furthermore be provided at the heating element or elements.

One or more pressure sensors can furthermore be provided to determine the pressure in the pump chambers. It can hereby be prevented that dialysate is pumped to the patient at too high a pressure or that the suction pressure becomes too high on the sucking of dialysate from the patient.

In the first embodiment, the pressure measurement takes place in this respect via pressure sensors in the hydraulic system of the pump actuators, as was shown above. In the second embodiment, in contrast, pressure sensors 85' and 86' are provided in the coupling surface which directly measure the pressure in corresponding pressure measurement regions of the cassette. The coupling of these pressure sensors to the cassette is in this respect advantageously ensured by a vacuum system.

2.6 Input/Output Unit

The dialysis machine furthermore includes an input/output unit for communication with an operator. A corresponding display is in this respect provided for the output of information which can e.g. be implemented by light-emitting diodes, LCD displays or a screen. Corresponding input elements are provided for the inputting of commands. Push buttons and switches can e.g. be provided in this respect.

In both embodiments, a touch screen 120 is provided in this respect which allows an interactive menu navigation. Display elements 121 and 122 are furthermore provided which show states of the dialysis machine in compact form.

The first embodiment furthermore has a card reader 125 via which a patient card can be read. Data on the treatment of the respective patient can be stored on the patient card. The treatment procedure for the respective patient can hereby be individually fixed.

The peritoneal dialysis furthermore has an acoustic signal unit via which acoustic signals can be output. In this respect, an acoustic warning signal can in particular be output when an error state is registered. A loudspeaker is in this respect advantageously provided via which the acoustic signals can be generated.

2.7 Controller

The peritoneal dialysis furthermore has a controller by which all components can be controlled and monitored. The controller in this respect provides the automatic procedure of the treatment.

The basic structure of an embodiment of such a controller is now shown in FIG. 13.

The communication with the operator and with external information sources in this respect takes place via an interface computer 150. It communicates with a patient card reader 200, an input and output unit 210 which serves communication with the patient and with a modem 220. Updated software can e.g. be uploaded via the modem.

The interface computer 150 is connected via an internal bus to an activity computer 160 and to a protective computer 170. The activity computer 160 and the protective computer 170 generate redundancy of the system. The activity computer 160 in this respect receives signals from the sensors of the system and calculates the control signals for the actuators 180. The protective computer 170 likewise receives signals from the sensors 180 and checks whether the commands output by the activity computer 160 are correct. If the protective computer 170 determines an error, it initiates a corresponding emergency procedure. The protective computer 170 can in particular trigger an alarm signal in this respect. The protective computer 170 can furthermore close the access to the patient. A special valve is arranged at the output of the cassette at the patient side for this purpose and only the protective computer 170 has access to it. This safety valve is in this respect closed in the pressureless state so that it closes automatically on a failure of the pneumatic system.

The protective computer 170 is furthermore connected to the barcode reader 190 and so checks the connection of the correct dialysis bags.

A diagnosis system 230 is furthermore provided via which errors of the system can be determined and remedied.

3. Implementation of the Invention

An embodiment of the present invention which is used in one of the dialysis systems presented above or in one of the dialysis machines presented above will now be presented in the following. In this respect, the embodiment of the present invention can be combined with individual components or a plurality of components, such as were described above.

An embodiment of a multi-chamber container is shown in FIG. 14 such as was already described in section 1.1 with respect to the embodiment of a dialysate container. The embodiment shown in FIG. 14 is in this respect advantageously likewise such a dialysate container.

In the embodiment, the multi-chamber container 300 in this respect has a first chamber 310 and a second chamber 320 which are separated from one another by a partition arrangement 330. In the first chamber 310, in this respect, a first individual solution is stored; a second individual solution is stored in the second solution 320. The partition arrangement 330 can be opened mechanically so that the two chambers 310 and 320 are in fluid communication with one another and the two individual solutions can thus be mixed to a total solution. The partition arrangement can in particular be opened manually by the patient or by an operator in this respect. The two chambers 310 and 320 in particular form a common, correspondingly larger chamber after the opening of the partition arrangement 330. Each of the two chambers 310 and 320 has a filling stub 315 and 325 respectively via which the respective chamber can be filled with an individual solution. The multi-chamber container 300 furthermore has an outflow 350 from which the total solution arising after opening the partition arrangement 330 can be removed. The outflow 350 is in this respect arranged in the region of the first chamber 310. If the partition arrangement 330 is therefore not opened, only fluid from the first chamber 310, i.e. the first individual solution, flows out of the outflow 350.

The partition arrangement 330 in the embodiment can be opened by the exertion of pressure onto at least one of the two chambers 310 or 320 filled with fluid. In the embodiment, the multi-chamber container is formed by a multi-chamber bag in this respect. It comprises two film layers 340 and 341 which are connected to one another, in particular welded to one another, in a marginal region. The partition arrangement 330 is in this respect formed by a so-called peel seam which extends from a first marginal region to a second marginal region of the bag and thus divides the bag into two chambers. In the region of the peel seam, the two film sections 340 and 341 are likewise connected to one another so that the multi-chamber bag allows a separate storage of the individual solutions. The connection in the region of the peel seam 330 is, however, designed such that it can be opened by pressure onto at least one of the chambers 310 or 320. The two chambers 310 and 320 are hereby connected to form a common larger chamber.

The outflow 350 is formed by a hose section which is welded between the two film layers 340 and 341 and is arranged in the region of the first chamber 310. The outflow 350 is in this respect usually equipped with a connector via which further components of the fluid system can be connected, in particular to a cassette.

A further peel seam can optionally be provided which first separates the outflow 350 from the first chamber or from the two chambers with individual solutions. Such a peel seam therefore has to be opened to be able to remove fluid form the bag at all and thus represents a further security element.

The multi-chamber bag 300 has at the oppositely disposed side of the outflow 350 a fastening element, e.g. in the form of a cut-out 360, at which the multi-chamber bag can e.g. be hung on a hook 370. This ensures that the outflow 350 is arranged at the lowest position of the bag and the fluid can thus completely flow out of the bag. For this purpose, the outflow 350 is arranged in a corner of the substantially rectangular bag; the cut-out or eyelet 360 is arranged in the oppositely disposed corner. The peel seam 330 in this respect extends so that, in the hung up state of the bag, the second chamber 320 is arranged at least partly higher than the first chamber 310. For this purpose, the peel seam 330 extends from one marginal region of the bag to a second marginal region of the bag, with the first and second marginal regions each being located between the region of the outflow 350 and the region of the cut-out or eyelet 360. In the embodiment, the peel seam 330 in this respect extends substantially parallel to a side of the rectangular bag.

A first embodiment of the present invention in which the dialysis machine automatically checks the proper opening of the partition arrangement 330 with reference to a pressure in the fluid system should now likewise be described in more detail with reference to FIG. 14. The checking of the proper opening in this respect takes place by the determination of the hydraulic pressure of the liquid from the multi-chamber container 300. The fluid system is for this purpose connected to the dialysis machine, whereby a pressure sensor is coupled to a pressure measurement region of the fluid system.

The measurement of the pressure in the fluid system can in this respect e.g. take place with reference to the pressure of a hydraulic fluid by which an actuator of the dialysis machine is moved or by a direct measurement of the pressure in a chamber of the cassette. The corresponding pressure measurement systems were already described in detail above.

A fluid connection between the pressure measurement region in the fluid system and the outflow 350 of the multi-chamber container 300 is now established by opening the corresponding valve regions in the fluid system by a corresponding control of the valve actuators of the dialysis machine. The pressure measurement can in this respect take place after filling at least a part of the fluid system.

The pressure which is exerted onto the pressure measurement region by the fluid column from the multi-chamber container is now determined in the stationary state of the system. Since the multi-chamber container 300 is arranged such that the fluid level in the first chamber 310 is lower with an unopened partition arrangement 330 than the fluid level with an opened partition arrangement in the forming common chamber, a different pressure results on the pressure measurement arrangement with a closed partition arrangement than after opening the partition arrangement. In the embodiment shown, a higher hydrostatic pressure will load on the pressure measurement region with an opened partition arrangement in this respect.

To ensure a reliable distinction between an opened and an unopened state of the partition arrangement, the multi-chamber container 300 should in this respect be arranged at a fixedly defined level with respect to the pressure measurement region of the fluid system. For this purpose, the multi-chamber container 300 can, e.g. as shown in FIG. 14, be hung at a hook 370 of a holder 380 which is in turn likewise connected to a rack 390. The dialysis machine is advantageously arranged on this rack so that an accurately defined position of the multi-chamber container 300 and the dialysis machine results.

In the arrangement shown in FIG. 14, the multi-chamber container 300 is in this respect arranged next to or above the dialysis machine. The present invention can, however, also be used in an arrangement such as is shown in FIG. 8. In this respect, the fluid level in the dialysate containers is below the pressure measurement region. To check the opening of the partition arrangement, fluid is therefore first pumped out of the multi-chamber container 300 into the fluid paths and the hydrostatic pressure of the fluid from the multi-chamber container 300 is then measured, which is negative in this case.

In a further embodiment, the partition arrangement can be opened automatically by the dialysis machine, and indeed by pressurization of a chamber of the multi-chamber container by the dialysis machine (automatic opening). The automatic opening can in this respect take place, on the one hand, via the pneumatic system of the dialysis machine, but, on the other hand, also by the pump actuators.

On the internal automatic application of pressure to the peel seam by the pneumatic system, outside air is necessary for the opening of the peel seam which has to be sucked in via a filter (sterility) and has to be pumped into the bag. This process is in particular of advantage when only one multi-chamber bag is used. To open the peel seam, a specific overpressure is necessary which lies in the region of 50 mbar (relative) with usual bags. The system generates such an overpressure in the chamber and so opens the peel seam.

The checking of the opening can take place as follows:
a) a pressure increase beyond the value required for the opening without a pressure drop having previously taken place can be evaluated by the system as an already opened bag. In this respect, a second limit value is preset which must naturally lie below the maximum permitted pressurization of the bag.
b) the characteristic of the pressure increase can be evaluated. i.e. with an opened peel seam in the bag, the pressure increase is slower than with a closed peel seam.

On the internal automatic application of pressure to the peel seam by the pump actuators, the fluid can be pumped from one bag into the other when two or more bags are used (standard case). Fluid can optionally also move from one chamber of the multi-chamber bag into another chamber, for which purpose the multi-chamber bags, however, require corresponding accesses. The pressure in the chamber becomes larger by the pumping of fluid into the chamber; the peel seam opens. A contamination by outside air is not given here. In this respect, the pumped volume and/or the pressure can be used for the control.

The monitoring of the opening can also take place via the pressure sensor system. The pressure drop within the bag which arises on the opening of the partition arrangement (usually in the range of 50 mbar) can be easily detected, in particular via the pressure sensor system associated with the pump chambers.

The following parameters can be taken into the check of the opening:
a) the characteristic of the pressure increase can be evaluated. i.e. with an opened peel seam in the bag, the pressure increase is slower than with a closed peel seam.
b) additional evaluation of the filling volume for the opening of the peel seam, i.e. after volume X, the peel seam must open in the bag and the pressure must drop.

The automatic opening of the partition arrangement can furthermore also be combined with other methods for the checking of the opening of the partition arrangement.

The automatic opening of the partition arrangement can in this respect also be taken care of in the filling procedure of the system. A conveying of the fluid into the other solution bags can be simply implemented here. Unmixed fluids which remain in the set after the opening of the partition arrangement could be conveyed into the drainage.

Figure 15A:
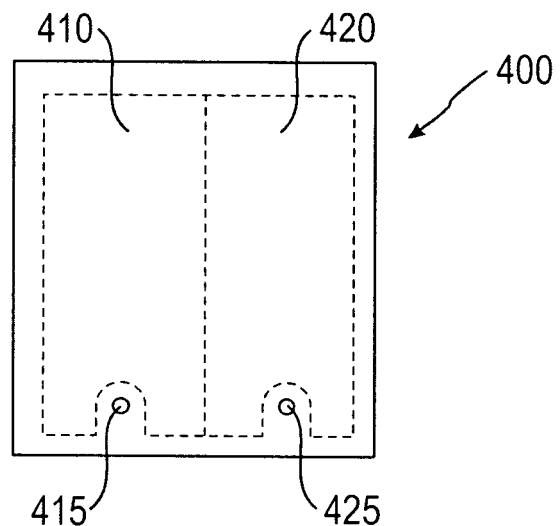
FIG. 15 an embodiment of a heating in accordance with an embodiment of the present invention.
Figure 15B:
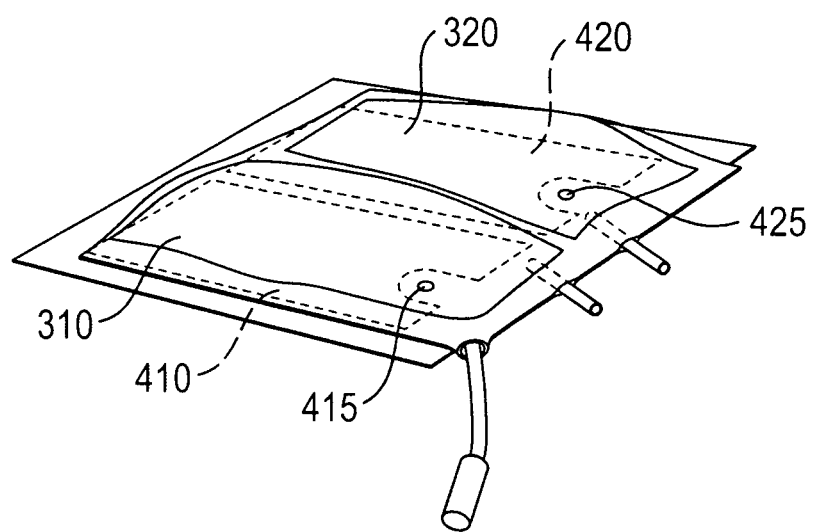

Two further embodiments of the present invention should now be shown in more detail with reference to FIGS. 15a and 15b. In this respect, the checking of the proper opening of the partition arrangement takes place via the determination of at least one temperature value of the fluid system.

In this respect, a heating arrangement 400 in accordance with an embodiment of the present invention is shown in 15a. The heating arrangement 400 in this respect has a heating surface to which the multi-chamber container can be coupled.

The coupling in this respect takes place in the simplest case by placing the multi-chamber container onto the heating surface. The heating surface can in this respect be arranged as was already shown in FIG. 8 with reference to the second embodiment of a dialysis machine shown there. The heating surface can in this respect in particular be integrated into a scale pan of the weighing device of the dialysis machine. Differently from there, however, it is not a separate heating bag, but rather the multi-chamber bag itself is placed onto the heating surface and heated. The heating surface now has a first heating region 410 and a second heating region 420. In this respect, at least the first heating region 410 can be heated separately from the second heating region 420. The heating regions 410 and 420 are designed in this respect such that the first heating region 410 is coupled to the first chamber 310 of the multi-chamber container and the second heating region 420 is coupled to the second chamber 320 of the multi-chamber container. As shown in FIG. 15b, this can be realized in that the first chamber 310 lies on the first heating region 410 whereas the second chamber 320 lies on the second heating region 420.

As shown above, the heating surface can be arranged substantially horizontally so that the multi-chamber bag lies on the heating surface and is held by it. Alternatively, the heating surface with the sensors can, however, also be arranged in the region of a bag suspension, with the multi-chamber bag contacting the heating surface. In this respect, a heating surface with temperature sensors integrated into a contact surface can be provided which is arranged below a hook for the hanging of the bag and which the bag contacts by gravity. The contact surface can in this respect be arranged perpendicular or slightly obliquely, with the bag contacting the contact surface by its arching. The association of the heating elements and sensors with the chambers of the bag in this respect takes place in the same manner as was shown above with respect to the substantially horizontally arranged heating surface. The two heating regions in this respect advantageously extend obliquely so that the multi-chamber bag can be hung at a corner and the two chambers hereby arranged obliquely are associated with the two heating regions.

In the above-described embodiments, the temperature sensors are integrated into the heating surface and have to be brought into contact with the multi-chamber bag. It is, however, also conceivable to arrange one or more temperature sensors directly at the multi-chamber bag. The temperature sensor or sensors can thus be reliably associated with the respective chambers. In this respect, the temperature sensor or sensors can be positioned at a point which does not come into contact with the heating elements, e.g. also at the wall of the bag disposed opposite the heating surface.

Such sensors can in particular be adhesively bonded to the multi-chamber bag or integrated into the multi-chamber bag in another manner. It is conceivable in this respect that the temperature sensors communicate in a wireless manner with the dialysis machine, in particular by radio. RFID chips can in particular be arranged for this purpose at the multi-chamber bag and the measured temperature values can be read out via them.

For the checking of the opening of the partition arrangement 330, only one of the two heating regions is now heated for a certain time period, e.g. only the first heating region 410. If the partition arrangement 330 was not opened, the heating surface 410 only heats the fluid in the first chamber 310. If, in contrast, the partition arrangement 330 was properly opened, the heating region 410 heats both the fluid from the first chamber 310 and the fluid from the second chamber 320 since the two chambers 310 and 310 are in communication with one another or form a common chamber.

A different temperature curve of the fluid hereby results in dependence on whether the partition arrangement was opened or not. The checking of the proper opening in this respect takes place with reference to a temperature sensor which is associated with one of the two chambers. In this respect, a temperature sensor 415 can be used which is associated with the first chamber 310 and/or a temperature sensor 425 which is associated with the second chamber 320. Both a first sensor 415 and a second sensor 425 are provided in this respect in the embodiment. The first sensor 415 is in this respect arranged on the heating surface 400 such that it is in contact with the region of the first chamber 310 of the multi-chamber container 300. The second sensor 425 is likewise arranged at the heating surface 400 so that it is in contact with the region of the second chamber 320.

In a first embodiment of the present invention, a check can now be made whether the liquid was heated in the region of the second chamber 320 even though only the first heating surface 410 associated with the first chamber 310 was heated. The temperature can thus e.g. be measured in the region of the second chamber 420 after a specific heating period and a check can be made whether it exceeds a specific limit value. It is equally conceivable first to determine a first temperature value and then to determine a second temperature value after a specific heating time and to check whether the difference is above a specific limit value. If the temperature or the temperature difference in the region of the second chamber remains below a preset limit value, this means that the partition arrangement was not opened properly.

Alternatively or additionally, the temperature of the first chamber 310 which is heated over the first heating surface 410 can also be determined. In this respect, a query can e.g. be made whether this temperature is above a limit value after a specific heating time. If this is the case, a conclusion can be made from this that the partition arrangement 330 was not opened. It is equally conceivable to determine the heating rate with reference to two or more measured values. If it is above a specific limit value, a conclusion can be made that the partition arrangement 330 was not opened.

The checking phase in which the multi-chamber container is only heated over one of the two heating regions can in this respect take place at the start of the activation phase of the dialysis machine. The total multi-chamber container is advantageously then heated with both heating regions after recognition of the proper opening.

In a further embodiment of the present invention, the proper opening of the partition arrangement 330 can also take place by a weighing cell integrated into the dialysis machine which determines the weight of a fluid container, in particular of the multi-chamber container. It can e.g. in this respect be a weighing cell such as is also used in the second embodiment shown in FIG. 8. The weighing cell in this respect measures the weight of the multi-chamber container. In this respect, the weighing cell can be combined with the heating surface so that the weight of the multi-chamber bag lying on the heating surface is measured. Alternatively, the weight of the multi-chamber bag can also be measured in the arrangement shown in FIG. 14 in that a weighing cell is arranged at the holder for the holding of the multi-chamber container.

The checking of the proper opening of the partition arrangement 330 in this respect advantageously takes place via the detection of the weight reduction over the time in the multi-chamber container. Conclusions can be drawn on the opening of the partition arrangement via the flow rate determined therefrom. Alternatively, the flow rate can also be determined by other balancing systems.

In a further embodiment of the present invention, an optical sensor is used which determines an optical property of the fluid in the multi-container or of the fluid taken from the multi-container.

The optical sensor can in this respect e.g. by a cloudiness sensor by which a color change of the fluid can be measured. In this respect, the individual solution is advantageously dyed with a biocompatible dye in the second chamber 320 which does not have an outflow 350. The fluid in the first chamber 310 with the outflow 350 is, in contrast, advantageously not dyed. A color change of the first individual solution 310 in this respect results from the opening of the partition arrangement 330 and the mixing of the two individual solutions. This can now be verified by a corresponding cloudiness sensor system.

It is equally conceivable that the individual solution in the chamber 310 has polarization properties differing from those of the total solution which is formed by mixing the individual solutions. The proper opening and mixing of the two individual solutions can therefore optionally also be verified by determining the polarization properties of the fluid in the bag or of the fluid removed from the bag.

Figure 16:
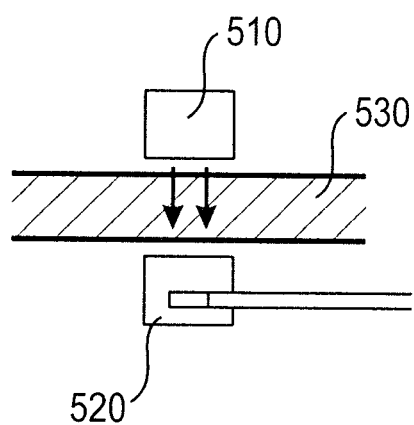
FIG. 16 an embodiment of an optical sensor in accordance with the present invention.

An embodiment of a corresponding optical sensor system is now shown in FIG. 16. In this respect, a light source 510 and an optical sensor 520 are provided. The two sensors are in this respect arranged so that a fluid path 530 is arranged between the light source 510 and the optical sensor 520 after the proper coupling of the fluid system. Fluid is now conducted from the multi-chamber container 300 into this fluid path 530 by a corresponding actuation of the valve regions of the fluid system.

The proper opening of the partition arrangement 330 is then checked by determination of an optical property of the liquid in the fluid path 530. The measurement region for the measurement of the optical property of the fluid can in this respect be arranged e.g. in a hose section of the fluid paths which therefore has to be coupled to the corresponding sensor region of the dialysis machine on the setting up. Alternatively, the measurement region can also be integrated into the cassette which is anyway coupled to a coupling surface of the dialysis machine. The sensor then measures the optical property of the liquid which is located in a corresponding measurement region of the cassette. In this respect, both sides of the cassette are advantageously transparent in this region and are advantageously further translucent.

If a color change should be determined, the optical sensor e.g. determines the light intensity of the light conducted through the fluid. If the polarization properties should be determined, the light source 510 advantageously transmits polarized light. The optical sensor 520 then advantageously measures the change in the polarization direction and/or the polarization type of the polarized light.

Figure 17:
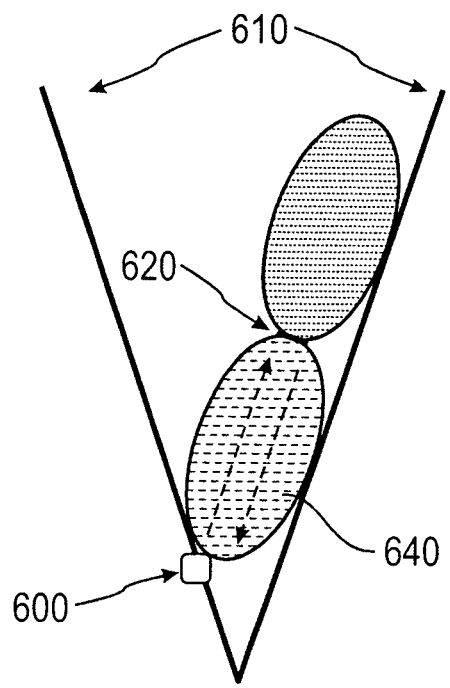
FIG. 17 a first embodiment of an ultrasonic sensor system in accordance with the present invention.
Figure 18:
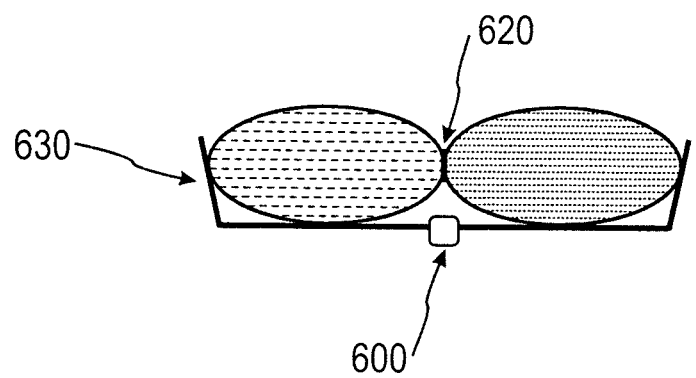
FIG. 18 a second embodiment of an ultrasonic sensor system in accordance with the present invention.

In a further embodiment of the dialysis machine in accordance with the invention, such as is shown in FIGS. 17 and 18, the check takes place by an ultrasonic sensor system, in particular via a reflection ultrasonic sensor system. The proper opening of the partition arrangement can in this respect take place by the detection of a reflection characteristic.

In FIG. 17, the ultrasonic sensor 600 is in this respect coupled to a first chamber 640 of the multi-chamber container on the coupling of the multi-chamber container to the dialysis machine. A conclusion can be drawn by the determination of the reflection characteristic of the chamber 640 of whether the partition arrangement 620 was opened or not since the size of the chamber depends on this. The checking can in this respect take place, on the one hand, with reference to an absolute value, e.g. on the filling level in the first chamber 640. Alternatively or additionally, the checking can also take place with reference to the change in the reflection characteristic by opening the partition arrangement. The method is therefore in particular easily suitable for the checking on an automatic opening of the partition arrangement by the dialysis machine.

In FIG. 17, the coupling of the sensor 600 to the chamber 640 in this respect takes place in that the sensor is arranged in the region of a heating arrangement 610 to which the multi-chamber bag is coupled. The heating arrangement in this respect has two heating plates 610 which are arranged in V shape, with the multi-chamber bag being hung up so that it lies in as large an area as possible on at least one of the plates. The sensor 600 is in this respect arranged on the other plate in a lower region so that the lower chamber 640 lies on the bag.

In FIG. 18, the ultrasonic sensor 600 is, in contrast, not coupled to the multi-chamber container after the coupling of the multi-chamber container to the dialysis machine with a closed partition arrangement 620 since the multi-chamber container is arranged in the region of the partition arrangement. A coupling of the multi-chamber bag to the sensor 600 only takes place when said partition arrangement is opened by the change in the shape of the multi-chamber bag associated therewith. Depending on the state of the partition arrangement, there are therefore considerably different reflection characteristics so that the checking of the proper opening can also take place with reference to the absolute values. A checking with reference to the change in the reflection characteristic can naturally likewise take place.

In FIG. 18, the sensor 600 is in this respect arranged in the region of the heating arrangement 6130 onto which the multi-chamber bag is placed. In the embodiment, the sensor is in this respect arranged approximately centrally since the partition arrangement is located in this region.

In the embodiments in FIGS. 17 and 18, a multi-chamber bag can be used such as was already described above.

In all embodiments of the present invention, the proper opening of the partition arrangement is advantageously checked before the liquid from the multi-chamber bag was used for the treatment of a patient. The check therefore in particular takes place in peritoneal dialysis before the dialysate was conducted from the multi-chamber bag to the patient. If the dialysis machine recognizes that the partition arrangement was not properly opened, it advantageously outputs a corresponding indication to the user. The indication can in this respect take place optically and/or acoustically. In this respect, an indication that the partition arrangement 330 has to be opened is advantageously presented on a display.

The machine in this respect only starts the treatment when the partition arrangement was properly opened and it is thus ensured that the dialysate used has the correct composition.

The present invention can admittedly optionally also be used in hemodialysis. However, multi-chamber containers with a corresponding partition arrangement are not customary there. In addition, the mixing from a plurality of containers carried out by the dialysis machine is there usually monitored by a conductivity sensor.

The present invention is therefore particularly advantageously used in peritoneal dialysis. The apparatus in accordance with the invention is therefore advantageously a peritoneal dialysis machine. In this respect, the checking of the proper opening of the partition arrangement advantageously takes place without the sensor being in direct contact with the fluid in the fluid paths.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis machine to which a fluid system having a multi-chamber container with at least two chambers with individual solutions separated by a partition arrangement to be opened mechanically can be coupled having a controller and at least one sensor for the determination of a measured variable in the fluid system, said dialysis machine comprising:
a heating element for heating of fluid in the multi-chamber container,
with the controller including an apparatus for automatic checking of proper opening of the partition arrangement of the multi-chamber container with reference to the measured variable determined by the sensor, and
with a first chamber of the multi-chamber container being heated for the checking of the proper opening of the partition arrangement of the multi-chamber container and a second chamber being not heated, and the checking being effected by determination of a temperature or of a temperature change in the fluid system.

2. The dialysis machine in accordance with claim 1, wherein the apparatus for the automatic checking checks the proper opening of the partition arrangement of the multi-chamber container before the fluid is removed from the multi-chamber container for a dialysis treatment, wherein the dialysis treatment only begins when the proper opening of the partition arrangement is recognized, and wherein otherwise a signal is output to a user.

3. The dialysis machine in accordance with claim 1, wherein the sensor measures the measured variable in the fluid system without direct contact with the fluid therein.

4. The dialysis machine in accordance with claim 3, further comprising at least one of a pressure sensor, a weight sensor, and an optical sensor.

5. The dialysis machine in accordance with claim 1, wherein the apparatus for the automatic checking automatically checks the proper opening of the partition arrangement of the multi-chamber container with reference to the change in the measured variable determined by the sensor over time.

6. The dialysis machine in accordance with claim 1, wherein the apparatus for the automatic checking of the proper opening of the partition arrangement of the multi-chamber container checks proper mixing of the individual solutions.

7. The dialysis machine in accordance with claim 1, wherein the sensor is at least one of a temperature sensor which is associated with the first chamber and via which the temperature of the fluid can be determined in the region of the first chamber and a temperature sensor which is associated with the second chamber and via which the temperature of the fluid in the region of the second chamber can be determined.

8. A dialysis machine in accordance with claim 1, wherein the checking takes place by determination of an optical property of the fluid in the fluid system; wherein the color and/or brightness and/or the polarization properties of the fluid in or out of the multi-chamber container is advantageously determined.

9. A dialysis machine in accordance with claim 1, wherein the checking is determined by determination of a pressure or of a pressure change in the fluid system, in particular with reference to the hydrostatic pressure of the fluid in or out of the multi-chamber container.

10. A dialysis machine in accordance with claim 1, wherein the checking takes place by determination of the weight and/or of the change in the weight of the multi-chamber container.

11. A dialysis machine in accordance with claim 1, wherein the checking is determined by determination of the flow rate of the fluid flowing out of the multi-chamber container.

12. A dialysis machine in accordance with claim 1, wherein the checking takes place by a ultrasonic sensor system, in particular via a reflection ultrasonic sensor system.

13. A dialysis machine in accordance with claim 12, wherein the checking takes place with reference to a change in the reflection characteristic which is caused by the opening of the partition arrangement.

14. The dialysis machine in accordance with claim 1, further comprising an element for automatic opening of the partition arrangement.

15. The dialysis machine in accordance with claim 14, wherein the element for the automatic opening of the partition arrangement includes an element for pressure build-up in at least one chamber of the multi-chamber container.

16. The dialysis machine in accordance with claim 14, wherein the apparatus for the automatic checking of the proper opening of the partition arrangement of the multi-chamber container checks the proper opening with reference to at least one of a pressure, a pressure development, and a filling quantity.

17. The dialysis machine in accordance with claim 1, wherein the dialysis machine is a peritoneal dialysis machine.

18. The dialysis machine in accordance with claim 2, wherein the apparatus for the automatic checking checks the proper opening of the partition arrangement of the multi-chamber container before the fluid is conducted to the patient.

19. The dialysis machine in accordance with claim 15, wherein the pressure build-up is effected by introduction of compressed air or by pumping of a fluid into the chamber.

* * * * *